(12) United States Patent
Molaei et al.

(10) Patent No.: US 9,687,245 B2
(45) Date of Patent: Jun. 27, 2017

(54) OCCLUSIVE DEVICES AND METHODS OF USE

(71) Applicant: Covidien LP, Mansfield, MA (US)

(72) Inventors: Masoud Molaei, Mountain View, CA (US); Michael Louis Losordo, San Juan Capistrano, CA (US); Ashok Nageswaran, Irvine, CA (US); Stephen Griffin, San Jose, CA (US); Jim Davidson, San Juan Capistrano, CA (US)

(73) Assignee: COVIDIEN LP, Mansfield, MA (US)

(*) Notice: Subject to any disclaimer, the term of this patent is extended or adjusted under 35 U.S.C. 154(b) by 209 days.

(21) Appl. No.: 13/841,836

(22) Filed: Mar. 15, 2013

(65) Prior Publication Data

US 2013/0253572 A1    Sep. 26, 2013

Related U.S. Application Data

(60) Provisional application No. 61/615,183, filed on Mar. 23, 2012, provisional application No. 61/616,406, filed on Mar. 27, 2012.

(51) Int. Cl.
*A61M 29/00* (2006.01)
*A61B 17/12* (2006.01)

(52) U.S. Cl.
CPC .. *A61B 17/12113* (2013.01); *A61B 17/12022* (2013.01); *A61B 17/12031* (2013.01);
(Continued)

(58) Field of Classification Search
CPC ........ A61B 17/12113; A61B 17/12022; A61B 17/1231; A61B 17/12118; A61B 17/12145; A61B 17/12172; A61B 17/1214; A61B 17/1215; A61B 17/12109; A61B 17/1219; A61B 2017/1205; A61B 2017/12054; A61B 2017/00867; A61B 2017/1215; A61F 2/95; A61F 2/88; A61F 2/013; A61F 2/01; A61F 2230/0006; A61F 2230/0069;
(Continued)

(56) References Cited

U.S. PATENT DOCUMENTS 3,334,629 A    8/1967   Colm
3,834,394 A    9/1974   Hunter et al.
(Continued)

FOREIGN PATENT DOCUMENTS

CA     2144725      5/1994
CA     2265062      9/1999
(Continued)

OTHER PUBLICATIONS

U.S. Appl. No. 13/764,028, filed Feb. 11, 2013.

*Primary Examiner* — Katherine M Shi
*Assistant Examiner* — Mohamed Gabr
(74) *Attorney, Agent, or Firm* — Beth McMahon

(57) ABSTRACT

An aneurysm therapy system, can include a catheter and an occlusive device. The catheter can have a proximal end, a distal end, and a lumen extending between the proximal and distal ends. The proximal end can include a self-expanding distal section, and the distal section can comprise a coil portion. The occlusive device can be disposed within the lumen and configured to reside in the aneurysm to restrict fluid flow within the aneurysm.

15 Claims, 13 Drawing Sheets

(52) U.S. Cl.
CPC ... *A61B 17/12118* (2013.01); *A61B 17/12145* (2013.01); *A61B 17/12172* (2013.01); *A61B 2017/1205* (2013.01); *A61B 2017/12054* (2013.01)

(58) Field of Classification Search
CPC ...... A61F 2230/0067; A61F 2230/0076; A61F 2230/0071; A61F 2230/008; A61F 2230/0091; A61F 2002/018; A61F 2002/016; A61F 2002/011; A61F 2002/9665; A61M 2025/09191
USPC ............... 606/200, 198, 194, 191, 159, 151
See application file for complete search history.

(56) References Cited

U.S. PATENT DOCUMENTS

| | | |
|---|---|---|
| 4,085,757 A | 4/1978 | Pevsner |
| 4,282,875 A | 8/1981 | Serbinenko et al. |
| 4,311,146 A | 1/1982 | Wonder |
| 4,327,734 A | 5/1982 | White, Jr. |
| 4,341,218 A | 7/1982 | U |
| 4,346,712 A | 8/1982 | Handa et al. |
| 4,364,392 A | 12/1982 | Strother et al. |
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,719,924 A | 1/1988 | Crittenden et al. |
| 4,735,201 A | 4/1988 | O'Reilly |
| 4,745,919 A | 5/1988 | Bundy et al. |
| 4,781,177 A | 11/1988 | Lebigot |
| 4,787,899 A | 11/1988 | Lazarus |
| 4,819,637 A | 4/1989 | Dormandy, Jr. et al. |
| 4,832,055 A | 5/1989 | Palestrant |
| 4,932,419 A | 6/1990 | de Toledo |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,304,194 A | 4/1994 | Chee et al. |
| 5,304,195 A | 4/1994 | Twyford, Jr. et al. |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A * | 1/1995 | Phelps ............ A61B 17/12022 604/907 |
| 5,382,260 A | 1/1995 | Dormandy, Jr. et al. |
| 5,382,261 A | 1/1995 | Palmaz |
| 5,397,345 A | 3/1995 | Lazarus |
| 5,417,708 A | 5/1995 | Hall et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,498,227 A | 3/1996 | Mawad |
| 5,507,769 A | 4/1996 | Marin et al. |
| 5,522,822 A | 6/1996 | Phelps et al. |
| 5,522,836 A | 6/1996 | Palermo |
| 5,527,338 A * | 6/1996 | Purdy ........................ 606/200 |
| 5,536,274 A | 7/1996 | Neuss |
| 5,540,680 A | 7/1996 | Guglielmi et al. |
| 5,549,624 A | 8/1996 | Mirigian et al. |
| 5,556,426 A | 9/1996 | Popadiuk et al. |
| 5,562,698 A | 10/1996 | Parker |
| 5,569,245 A | 10/1996 | Guglielmi et al. |
| 5,573,520 A | 11/1996 | Schwartz et al. |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A * | 11/1997 | Berenstein et al. ........... 606/191 |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,792,157 A * | 8/1998 | Mische ............ A61B 17/32072 606/159 |
| 5,797,953 A | 8/1998 | Tekulve |
| 5,800,426 A | 9/1998 | Taki et al. |
| 5,800,453 A | 9/1998 | Gia |
| 5,800,454 A | 9/1998 | Jacobsen et al. |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,130 A | 4/1999 | Palermo et al. |

(56) References Cited

U.S. PATENT DOCUMENTS

| | | |
|---|---|---|
| 5,891,155 A | 4/1999 | Irie |
| 5,891,192 A | 4/1999 | Murayama et al. |
| 5,895,385 A | 4/1999 | Guglielmi et al. |
| 5,895,391 A | 4/1999 | Farnholtz |
| 5,895,410 A | 4/1999 | Forber et al. |
| 5,895,411 A | 4/1999 | Irie |
| 5,911,731 A | 6/1999 | Pham et al. |
| 5,911,737 A | 6/1999 | Lee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglielmi |
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |
| 5,976,152 A | 11/1999 | Regan et al. |
| 5,976,162 A | 11/1999 | Doan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,929 A | 11/1999 | Bashiri et al. |
| 5,984,944 A | 11/1999 | Forber |
| 5,989,242 A | 11/1999 | Saadat et al. |
| 6,001,092 A | 12/1999 | Mirigian et al. |
| 6,004,338 A | 12/1999 | Ken et al. |
| 6,010,498 A | 1/2000 | Guglielmi |
| 6,013,084 A | 1/2000 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,019,779 A | 2/2000 | Thorud et al. |
| 6,022,369 A | 2/2000 | Jacobsen et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,070 A | 5/2000 | Eder |
| 6,063,100 A | 5/2000 | Diaz et al. |
| 6,063,104 A | 5/2000 | Villar et al. |
| 6,066,133 A | 5/2000 | Guglielmi et al. |
| 6,066,149 A | 5/2000 | Samson et al. |
| 6,066,158 A * | 5/2000 | Engelson ............ A61B 17/221 606/159 |
| 6,068,644 A | 5/2000 | Lulo et al. |
| 6,074,407 A | 6/2000 | Levine et al. |
| 6,077,260 A | 6/2000 | Wheelock et al. |
| D427,680 S | 7/2000 | Mariant et al. |
| 6,083,220 A | 7/2000 | Guglielmi et al. |
| 6,086,577 A | 7/2000 | Ken et al. |
| 6,090,125 A | 7/2000 | Horton |
| 6,093,199 A | 7/2000 | Brown et al. |
| 6,096,034 A | 8/2000 | Kupiecki et al. |
| 6,096,546 A | 8/2000 | Raskin |
| 6,102,917 A | 8/2000 | Maitland et al. |
| 6,102,932 A | 8/2000 | Kurz |
| 6,102,933 A | 8/2000 | Lee et al. |
| 6,113,622 A | 9/2000 | Hieshima |
| 6,117,142 A | 9/2000 | Goodson et al. |
| 6,117,157 A | 9/2000 | Tekulve |
| 6,123,714 A | 9/2000 | Gia et al. |
| 6,126,672 A | 10/2000 | Berryman et al. |
| 6,136,015 A | 10/2000 | Kurz et al. |
| 6,143,007 A | 11/2000 | Mariant et al. |
| 6,146,373 A | 11/2000 | Cragg et al. |
| 6,149,664 A | 11/2000 | Kurz |
| 6,149,681 A | 11/2000 | Houser et al. |
| 6,156,061 A | 12/2000 | Wallace et al. |
| 6,159,165 A | 12/2000 | Ferrera et al. |
| 6,159,206 A | 12/2000 | Ogawa |
| 6,165,178 A | 12/2000 | Bashiri et al. |
| 6,165,193 A | 12/2000 | Greene, Jr. et al. |
| 6,165,198 A | 12/2000 | McGurk et al. |
| 6,168,570 B1 | 1/2001 | Ferrera |
| 6,168,592 B1 | 1/2001 | Kupiecki et al. |
| 6,168,610 B1 | 1/2001 | Marin et al. |
| 6,168,615 B1 | 1/2001 | Ken et al. |
| 6,168,622 B1 | 1/2001 | Mazzocchi |
| 6,171,326 B1 | 1/2001 | Ferrera et al. |
| 6,183,491 B1 | 2/2001 | Lulo |
| 6,183,495 B1 | 2/2001 | Lenker et al. |
| 6,187,024 B1 | 2/2001 | Boock et al. |
| 6,187,027 B1 | 2/2001 | Mariant et al. |
| 6,190,373 B1 | 2/2001 | Palermo et al. |
| 6,193,708 B1 | 2/2001 | Ken et al. |
| 6,193,728 B1 | 2/2001 | Ken et al. |
| RE37,117 E | 3/2001 | Palermo |
| 6,202,261 B1 | 3/2001 | Moore et al. |
| 6,203,547 B1 | 3/2001 | Nguyen et al. |
| 6,221,066 B1 | 4/2001 | Ferrera et al. |
| 6,221,086 B1 | 4/2001 | Forber |
| 6,224,610 B1 | 5/2001 | Ferrera |
| 6,231,573 B1 | 5/2001 | Amor et al. |
| 6,231,586 B1 | 5/2001 | Mariant |
| 6,231,590 B1 | 5/2001 | Slaikeu et al. |
| 6,231,597 B1 | 5/2001 | Deem et al. |
| 6,238,403 B1 * | 5/2001 | Greene, Jr. ...... A61B 17/12022 606/108 |
| 6,238,415 B1 | 5/2001 | Sepetka et al. |
| 6,241,691 B1 | 6/2001 | Ferrera et al. |
| 6,254,592 B1 | 7/2001 | Samson et al. |
| 6,254,628 B1 | 7/2001 | Wallace et al. |
| 6,270,495 B1 | 8/2001 | Palermo |
| 6,277,125 B1 | 8/2001 | Barry et al. |
| 6,277,126 B1 | 8/2001 | Barry et al. |
| 6,280,457 B1 | 8/2001 | Wallace et al. |
| 6,281,263 B1 | 8/2001 | Evans et al. |
| 6,287,315 B1 | 9/2001 | Wijeratne et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,299,627 B1 | 10/2001 | Eder et al. |
| 6,306,153 B1 | 10/2001 | Kurz et al. |
| 6,312,405 B1 | 11/2001 | Meyer et al. |
| 6,312,421 B1 | 11/2001 | Boock |
| 6,315,709 B1 | 11/2001 | Garibaldi et al. |
| 6,319,267 B1 | 11/2001 | Kurz |
| 6,322,576 B1 | 11/2001 | Wallace et al. |
| 6,328,750 B1 | 12/2001 | Berry et al. |
| 6,331,184 B1 | 12/2001 | Abrams |
| 6,335,384 B1 | 1/2002 | Evans et al. |
| 6,338,736 B1 | 1/2002 | Boosfeld et al. |
| 6,344,041 B1 | 2/2002 | Kupiecki et al. |
| 6,344,048 B1 | 2/2002 | Chin et al. |
| 6,346,091 B1 | 2/2002 | Jacobsen et al. |
| 6,346,117 B1 * | 2/2002 | Greenhalgh ...... A61B 17/12022 606/200 |
| 6,348,041 B1 | 2/2002 | Klint |
| 6,361,547 B1 | 3/2002 | Hieshima |
| 6,364,823 B1 | 4/2002 | Garibaldi et al. |
| 6,368,338 B1 | 4/2002 | Konya et al. |
| 6,371,972 B1 | 4/2002 | Wallace et al. |
| 6,375,606 B1 | 4/2002 | Garibaldi et al. |
| 6,375,628 B1 | 4/2002 | Zadno-Azizi et al. |
| 6,375,668 B1 | 4/2002 | Gifford et al. |
| 6,375,669 B1 | 4/2002 | Rosenbluth et al. |

(56) References Cited

U.S. PATENT DOCUMENTS

| | | |
|---|---|---|
| 6,379,329 B1 | 4/2002 | Naglreiter et al. |
| 6,379,374 B1 | 4/2002 | Hieshima et al. |
| 6,383,146 B1 | 5/2002 | Klint |
| 6,383,174 B1 | 5/2002 | Eder |
| 6,383,204 B1 | 5/2002 | Ferrera et al. |
| 6,383,205 B1 | 5/2002 | Samson et al. |
| 6,409,721 B1 | 6/2002 | Wheelock et al. |
| 6,416,535 B1 | 7/2002 | Lazarus |
| 6,416,541 B2 | 7/2002 | Denardo |
| 6,423,085 B1 | 7/2002 | Murayama et al. |
| 6,425,893 B1 | 7/2002 | Guglielmi |
| 6,425,914 B1 | 7/2002 | Wallace et al. |
| 6,428,557 B1 | 8/2002 | Hilaire |
| 6,428,558 B1 | 8/2002 | Jones et al. |
| 6,454,780 B1 | 9/2002 | Wallace |
| 6,458,119 B1 | 10/2002 | Berenstein et al. |
| 6,458,127 B1 | 10/2002 | Truckai et al. |
| 6,458,137 B1 | 10/2002 | Klint |
| 6,464,699 B1 | 10/2002 | Swanson |
| 6,468,266 B1 | 10/2002 | Bashiri et al. |
| 6,475,169 B2 | 11/2002 | Ferrera |
| 6,475,227 B2 | 11/2002 | Burke et al. |
| 6,478,773 B1 | 11/2002 | Gandhi et al. |
| 6,485,524 B2 | 11/2002 | Strecker |
| 6,494,884 B2 | 12/2002 | Gifford, III et al. |
| 6,500,149 B2 | 12/2002 | Gandhi et al. |
| 6,500,190 B2 | 12/2002 | Greene, Jr. et al. |
| 6,506,204 B2 | 1/2003 | Mazzocchi |
| 6,511,468 B1 | 1/2003 | Cragg et al. |
| 6,514,264 B1 | 2/2003 | Naglreiter |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross, III et al. |
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh |
| 6,547,804 B2 | 4/2003 | Porter et al. |
| 6,551,305 B2 | 4/2003 | Ferrera et al. |
| 6,551,340 B1 | 4/2003 | Konya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Klint |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,605 B2 | 7/2003 | Lenker et al. |
| 6,602,261 B2 | 8/2003 | Greene, Jr. et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,616,617 B1 | 9/2003 | Ferrera et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | Makower et al. |
| 6,656,173 B1 | 12/2003 | Palermo |
| 6,656,201 B2 | 12/2003 | Ferrera et al. |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,679,903 B2 | 1/2004 | Kurz |
| 6,685,653 B2 | 2/2004 | Ehr et al. |
| 6,685,696 B2 | 2/2004 | Fleischhacker et al. |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshima |
| 6,964,657 B2 | 11/2005 | Cragg et al. |
| 6,966,892 B2 | 11/2005 | Gandhi et al. |
| 6,984,240 B1 | 1/2006 | Ken et al. |
| 6,994,689 B1 * | 2/2006 | Zadno-Azizi .... A61B 17/12022 604/103.03 |
| 6,994,711 B2 | 2/2006 | Hieshima et al. |
| 7,014,645 B2 | 3/2006 | Greene, Jr. et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,147,618 B2 | 12/2006 | Kurz |
| 7,169,161 B2 | 1/2007 | Bonnette et al. |
| 7,182,774 B2 | 2/2007 | Barry et al. |
| 7,198,613 B2 | 4/2007 | Gandhi et al. |
| 7,238,194 B2 | 7/2007 | Monstadt et al. |
| 7,300,458 B2 | 11/2007 | Henkes et al. |
| 7,316,701 B2 | 1/2008 | Ferrera et al. |
| 7,323,000 B2 | 1/2008 | Monstdt et al. |
| 7,331,973 B2 | 2/2008 | Gesswein et al. |
| 7,344,558 B2 | 3/2008 | Lorenzo et al. |
| 7,410,482 B2 | 8/2008 | Murphy et al. |
| 7,473,266 B2 | 1/2009 | Glaser |
| 7,485,122 B2 | 2/2009 | Teoh |
| 7,485,317 B1 | 2/2009 | Murayama et al. |
| 7,524,322 B2 | 4/2009 | Monstdt et al. |
| 7,575,582 B2 | 8/2009 | Gandhi et al. |
| 7,578,826 B2 | 8/2009 | Gandhi et al. |
| RE41,029 E | 12/2009 | Guglielmi et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,766,933 B2 | 8/2010 | Davis, III et al. |
| 7,811,305 B2 | 10/2010 | Balgobin et al. |
| 7,841,994 B2 | 11/2010 | Skujins et al. |
| 7,879,064 B2 | 2/2011 | Monstadt et al. |
| 7,883,526 B2 | 2/2011 | Jones et al. |
| 7,896,899 B2 | 3/2011 | Patterson et al. |
| 7,901,444 B2 | 3/2011 | Slazas |
| 7,901,704 B2 | 3/2011 | Richard |
| 7,918,872 B2 | 4/2011 | Mitelberg et al. |
| 7,938,845 B2 | 5/2011 | Aganon et al. |
| 7,955,272 B2 | 6/2011 | Rooney et al. |
| 8,002,789 B2 | 8/2011 | Ramzipoor et al. |
| 8,007,509 B2 | 8/2011 | Buiser et al. |
| 8,372,110 B2 | 2/2013 | Monstadt et al. |
| 2002/0010481 A1 | 1/2002 | Jayaraman |

(56) References Cited

U.S. PATENT DOCUMENTS

| | | |
|---|---|---|
| 2002/0019647 A1 | 2/2002 | Wallace et al. |
| 2002/0052613 A1 | 5/2002 | Ferrera et al. |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0045901 A1 | 3/2003 | Opolski |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0176857 A1 | 9/2003 | Lee |
| 2003/0181927 A1 | 9/2003 | Wallace |
| 2003/0216772 A1 | 11/2003 | Konya et al. |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1 | 1/2004 | Teoh |
| 2004/0006354 A1 | 1/2004 | Schaefer et al. |
| 2004/0006362 A1 | 1/2004 | Schaefer et al. |
| 2004/0006363 A1 | 1/2004 | Schaefer |
| 2004/0024394 A1 | 2/2004 | Wallace et al. |
| 2004/0034363 A1 | 2/2004 | Wilson et al. |
| 2004/0034378 A1 | 2/2004 | Monstadt et al. |
| 2004/0045554 A1 | 3/2004 | Schaefer et al. |
| 2004/0078050 A1 | 4/2004 | Monstadt et al. |
| 2004/0082879 A1 | 4/2004 | Klint |
| 2004/0106946 A1 | 6/2004 | Ferrera et al. |
| 2004/0181256 A1 | 9/2004 | Glaser |
| 2004/0193178 A1 | 9/2004 | Nikolchev |
| 2004/0193206 A1 | 9/2004 | Gerberding et al. |
| 2004/0220563 A1 | 11/2004 | Eder |
| 2004/0220585 A1 | 11/2004 | Nikolchev |
| 2004/0225279 A1 | 11/2004 | Raymond |
| 2004/0236344 A1 | 11/2004 | Monstadt et al. |
| 2004/0260384 A1 | 12/2004 | Allen |
| 2005/0021023 A1 | 1/2005 | Guglielmi et al. |
| 2005/0021074 A1 | 1/2005 | Elliott |
| 2005/0079196 A1 | 4/2005 | Henkes et al. |
| 2005/0171572 A1 | 8/2005 | Martinez |
| 2005/0177185 A1 | 8/2005 | Becker et al. |
| 2005/0187564 A1 | 8/2005 | Jayaraman |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116711 A1 | 6/2006 | Elliott et al. |
| 2006/0116713 A1* | 6/2006 | Sepetka et al. ............... 606/200 |
| 2006/0116714 A1 | 6/2006 | Sepetka et al. |
| 2006/0200190 A1 | 9/2006 | Lorenzo et al. |
| 2006/0253148 A1 | 11/2006 | Leone et al. |
| 2006/0271097 A1 | 11/2006 | Ramzipoor et al. |
| 2006/0276824 A1 | 12/2006 | Mitelberg et al. |
| 2007/0055302 A1 | 3/2007 | Henry et al. |
| 2007/0083226 A1 | 4/2007 | Buiser et al. |
| 2007/0142893 A1 | 6/2007 | Buiser et al. |
| 2007/0150045 A1 | 6/2007 | Ferrera |
| 2007/0173757 A1 | 7/2007 | Levine et al. |
| 2007/0185524 A1 | 8/2007 | Diaz et al. |
| 2007/0225738 A1 | 9/2007 | Pal |
| 2007/0239193 A1 | 10/2007 | Simon et al. |
| 2007/0239199 A1 | 10/2007 | Jayaraman |
| 2007/0265656 A1* | 11/2007 | Amplatz ............ A61B 17/0057 606/200 |
| 2007/0282425 A1 | 12/2007 | Kleine et al. |
| 2007/0299461 A1 | 12/2007 | Elliott |
| 2008/0045922 A1 | 2/2008 | Cragg et al. |
| 2008/0046092 A1 | 2/2008 | Davis et al. |
| 2008/0046093 A1 | 2/2008 | Davis et al. |
| 2008/0051803 A1 | 2/2008 | Monjtadt et al. |
| 2008/0097401 A1* | 4/2008 | Trapp ............... A61B 17/12022 604/527 |
| 2008/0097462 A1 | 4/2008 | Mitelberg et al. |
| 2008/0097508 A1* | 4/2008 | Jones ............... A61B 17/12022 606/191 |
| 2008/0103585 A1 | 5/2008 | Monstadt et al. |
| 2008/0125855 A1 | 5/2008 | Henkes et al. |
| 2008/0228215 A1 | 9/2008 | Strauss et al. |
| 2008/0228216 A1 | 9/2008 | Strauss et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0025820 A1* | 1/2009 | Adams ............ A61B 17/12022 140/71 C |
| 2009/0048631 A1 | 2/2009 | Bhatnagar et al. |
| 2009/0069836 A1 | 3/2009 | Labdag et al. |
| 2009/0149864 A1 | 6/2009 | Porter |
| 2009/0182268 A1 | 7/2009 | Thielen et al. |
| 2009/0254111 A1 | 10/2009 | Monstadt et al. |
| 2009/0254169 A1 | 10/2009 | Spenser et al. |
| 2009/0270877 A1 | 10/2009 | Johnson et al. |
| 2009/0312748 A1 | 12/2009 | Johnson et al. |
| 2010/0004673 A1 | 1/2010 | Denison et al. |
| 2010/0004675 A1 | 1/2010 | Wilson et al. |
| 2010/0023105 A1 | 1/2010 | Levy et al. |
| 2010/0030200 A1 | 2/2010 | Strauss et al. |
| 2010/0030319 A1 | 2/2010 | Weber |
| 2010/0049165 A1 | 2/2010 | Sutherland et al. |
| 2010/0076479 A1 | 3/2010 | Monstadt |
| 2010/0174269 A1 | 7/2010 | Tompkins et al. |
| 2011/0022003 A1 | 1/2011 | Tekulve |
| 2011/0082493 A1* | 4/2011 | Samson ............... A61B 17/221 606/200 |
| 2011/0098814 A1 | 4/2011 | Monstadt et al. |
| 2011/0118777 A1 | 5/2011 | Patterson et al. |
| 2011/0172700 A1 | 7/2011 | Bose et al. |
| 2011/0184454 A1 | 7/2011 | Barry et al. |
| 2011/0213405 A1* | 9/2011 | Porter ............... A61B 17/12022 606/200 |
| 2011/0213406 A1 | 9/2011 | Aganon et al. |
| 2011/0245861 A1 | 10/2011 | Chen et al. |
| 2011/0303447 A1 | 12/2011 | Strauss et al. |
| 2011/0313447 A1 | 12/2011 | Strauss et al. |
| 2013/0116722 A1* | 5/2013 | Aboytes ............... A61M 29/00 606/198 |
| 2013/0190801 A1 | 7/2013 | Divino et al. |
| 2013/0253572 A1 | 9/2013 | Molaei et al. |

FOREIGN PATENT DOCUMENTS

| | | |
|---|---|---|
| CN | 1668250 A | 9/2005 |
| DE | 4445715 | 6/1996 |
| DE | 69627243 | 1/1997 |
| DE | 19547617 | 9/1997 |
| DE | 19607451 | 9/1997 |
| DE | 19610333 | 9/1997 |
| DE | 19647280 | 5/2001 |
| DE | 19952387 | 5/2001 |
| DE | 10010840 | 9/2001 |
| DE | 10118017 | 10/2002 |
| DE | 10155191 | 5/2003 |
| EP | 707830 | 4/1996 |
| EP | 711 532 | 5/1996 |
| EP | 717969 A2 | 6/1996 |
| EP | 720838 | 7/1996 |
| EP | 765636 | 4/1997 |
| EP | 792623 | 9/1997 |
| EP | 820726 | 1/1998 |
| EP | 829236 | 3/1998 |
| EP | 830873 | 3/1998 |
| EP | 853955 | 7/1998 |
| EP | 865773 | 9/1998 |
| EP | 882428 | 9/1998 |
| EP | 904737 | 3/1999 |
| EP | 914807 | 5/1999 |

(56) References Cited

FOREIGN PATENT DOCUMENTS

| | | |
|---|---|---|
| EP | 941700 | 9/1999 |
| EP | 941701 | 9/1999 |
| EP | 992220 | 4/2000 |
| EP | 1005837 A2 | 6/2000 |
| EP | 1120088 | 8/2001 |
| EP | 1125553 | 8/2001 |
| EP | 1129666 | 9/2001 |
| EP | 1142535 | 10/2001 |
| EP | 1169969 | 1/2002 |
| EP | 1188413 | 3/2002 |
| EP | 1188414 | 3/2002 |
| EP | 1295563 | 3/2003 |
| EP | 1312312 | 5/2003 |
| EP | 1316293 | 6/2003 |
| EP | 1358850 | 11/2003 |
| EP | 1374801 | 1/2004 |
| EP | 1669032 | 6/2006 |
| EP | 1738698 A2 | 1/2007 |
| EP | 832607 | 4/2008 |
| EP | 2260800 A2 | 12/2010 |
| EP | 2292147 | 3/2011 |
| JP | 6-246004 | 9/1994 |
| JP | 7-155331 | 6/1995 |
| JP | 7-265431 | 10/1995 |
| JP | 7-284534 | 10/1995 |
| JP | 9-168541 A | 6/1997 |
| JP | 10-201766 | 8/1998 |
| JP | 11-47138 | 2/1999 |
| JP | 11-76249 | 3/1999 |
| JP | 2001-513389 A | 9/2001 |
| JP | 2002-523172 A | 7/2002 |
| JP | 2004-500929 A | 1/2004 |
| JP | 2006-051349 A | 2/2006 |
| JP | 2008-525113 A | 7/2008 |
| KR | 10-2010-107255 | 10/2010 |
| KR | 10-1014547 | 2/2011 |
| WO | WO-88/03817 | 6/1988 |
| WO | WO-89/06984 | 8/1989 |
| WO | WO-90/12616 | 11/1990 |
| WO | WO-91/13592 | 9/1991 |
| WO | WO-92/14408 | 9/1992 |
| WO | WO-92/21400 | 12/1992 |
| WO | WO-93/11719 | 6/1993 |
| WO | WO-93/16650 | 9/1993 |
| WO | WO-94/06502 A2 | 3/1994 |
| WO | WO-94/06503 | 3/1994 |
| WO | WO-94/10936 | 5/1994 |
| WO | WO-94/11051 | 5/1994 |
| WO | WO-94/26175 | 11/1994 |
| WO | WO-95/12367 | 5/1995 |
| WO | WO-96/18343 | 6/1996 |
| WO | WO-96/32153 | 10/1996 |
| WO | WO-96/39950 | 12/1996 |
| WO | WO-97/27888 | 8/1997 |
| WO | WO-97/42881 | 11/1997 |
| WO | WO-98/09570 | 3/1998 |
| WO | WO-98/17183 | 4/1998 |
| WO | WO-98/33452 | 8/1998 |
| WO | WO-98/34546 | 8/1998 |
| WO | WO-98/39048 A2 | 9/1998 |
| WO | WO-98/58590 | 12/1998 |
| WO | WO-99/02094 | 1/1999 |
| WO | WO-99/05977 | 2/1999 |
| WO | WO-99/07292 | 2/1999 |
| WO | WO-99/09893 | 3/1999 |
| WO | WO-99/32037 | 7/1999 |
| WO | WO-99/42038 | 8/1999 |
| WO | WO-99/44538 | 9/1999 |
| WO | WO-99/49812 A2 | 10/1999 |
| WO | WO-99/56636 | 11/1999 |
| WO | WO-00/12016 | 3/2000 |
| WO | WO-00/13593 | 3/2000 |
| WO | WO-00/25680 | 5/2000 |
| WO | WO-00/44306 | 8/2000 |
| WO | WO-00/72781 A2 | 12/2000 |
| WO | WO-01/32085 | 5/2001 |
| WO | WO-01/45571 A1 | 6/2001 |
| WO | WO-01/56500 A2 | 8/2001 |
| WO | WO-01/58365 | 8/2001 |
| WO | WO-01/58382 A2 | 8/2001 |
| WO | WO-01/87184 | 11/2001 |
| WO | WO-01/93937 A2 | 12/2001 |
| WO | WO-02/02018 | 1/2002 |
| WO | WO-02/13705 | 2/2002 |
| WO | WO-02/13706 A2 | 2/2002 |
| WO | WO-02/32496 | 4/2002 |
| WO | WO-02/39911 A2 | 5/2002 |
| WO | WO-02/41753 A2 | 5/2002 |
| WO | WO-02/45596 A2 | 6/2002 |
| WO | WO-02/054943 A2 | 7/2002 |
| WO | WO-02/054980 A2 | 7/2002 |
| WO | WO-02/072168 A2 | 9/2002 |
| WO | WO-02/087449 | 11/2002 |
| WO | WO-02/087651 | 11/2002 |
| WO | WO-02/089676 A2 | 11/2002 |
| WO | WO-02/096273 A2 | 12/2002 |
| WO | WO-02/096301 | 12/2002 |
| WO | WO-03/001970 A2 | 1/2003 |
| WO | WO-03/007823 | 1/2003 |
| WO | WO-03/017852 | 3/2003 |
| WO | WO-03/034927 | 5/2003 |
| WO | WO-03/039624 A2 | 5/2003 |
| WO | WO-03/041615 | 5/2003 |
| WO | WO-03/053257 | 7/2003 |
| WO | WO-03/053281 | 7/2003 |
| WO | WO-03/073914 A2 | 9/2003 |
| WO | WO-03/077776 | 9/2003 |
| WO | WO-03/077984 | 9/2003 |
| WO | WO-03/082128 | 10/2003 |
| WO | WO-03/086240 | 10/2003 |
| WO | WO-03/092547 | 11/2003 |
| WO | WO-03/099370 | 12/2003 |
| WO | WO-2004/008974 | 1/2004 |
| WO | WO-2004/010878 A1 | 2/2004 |
| WO | WO-2004/014239 | 2/2004 |
| WO | WO-2004/069059 | 8/2004 |
| WO | WO-2004/073529 | 9/2004 |
| WO | WO-2005/065556 | 7/2005 |
| WO | WO-2006/058042 A2 | 6/2006 |
| WO | WO-2006/069123 | 6/2006 |
| WO | WO-2007/121405 | 10/2007 |
| WO | WO-2008/112435 | 9/2008 |
| WO | WO-2008/112436 | 9/2008 |
| WO | WO-2008/127328 | 10/2008 |
| WO | WO-2010/092174 A2 | 8/2010 |
| WO | WO-2010/117883 | 10/2010 |
| WO | WO-2010/123821 | 10/2010 |
| WO | WO-2010/134914 | 11/2010 |
| WO | WO-2011/030820 | 3/2011 |
| WO | WO-2012/034135 A1 | 3/2012 |
| WO | WO-2012/161953 A2 | 11/2012 |

\* cited by examiner

OCCLUSIVE DEVICES AND METHODS OF USE

CROSS-REFERENCE TO RELATED APPLICATIONS

The present application claims priority benefit of U.S. Provisional Patent Application Nos. 61/616,406, filed Mar. 27, 2012, titled OCCLUSIVE DEVICE, and 61/615,183, filed Mar. 23, 2012, titled OCCLUSIVE DEVICE, the entire contents of each of which are incorporated by reference herein.

BACKGROUND

Field of the Inventions

The present disclosures relate to implantable devices. More specifically, the present disclosures relate to occlusive devices that can be implanted endovascularly, and in some embodiments, for aneurysm therapy.

Description of the Related Art

Numerous embolization devices have been provided for aneurysm treatment. Generally, braid-ball embolic devices, coils, and other types of embolization operate through blood flow disruption and subsequent thrombus formation.

SUMMARY

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

In accordance with some embodiments, an aneurysm therapy system and methods of treating an aneurysm can be provided. The system can comprise a catheter and an occlusive device. The catheter can have a proximal end, a distal end, and a lumen extending between the proximal and distal ends. The occlusive device can be disposed within the lumen and configured to reside in the aneurysm to restrict fluid flow within the aneurysm.

The device can comprise a distal section and a self-expanding proximal portion. The distal section can comprise a coil having an outer diameter, a coil length, and a coil flexibility. Further, the proximal section can have (i) a radially compressed state with a first diameter when positioned within the delivery lumen and (ii) a radially expanded state with a second diameter, greater than the coil diameter, when unconstrained, (iii) a braid length greater than the coil length, and (iv) a braid flexibility less than the coil flexibility per unit length.

In some embodiments, the proximal section can be configured to expand during advancement out of the distal end of the catheter, and the distal section can be configured to distribute, along at least a portion of the coil length, a force of the advancement along an aneurysm interior wall.

Further, in some embodiments, the device can optionally comprise a transition section, between the proximal and distal sections, that has a lower flexibility per unit length than the coil flexibility and the braid flexibility.

The distal section can be configured to abut the aneurysm interior wall to direct the distalmost proximal section as the proximal section is advanced into the aneurysm. The distal section can comprise a curved distal end. For example, a maximum radius of curvature of the distal section can be less than a maximum radius of curvature of the proximal section.

The distal section can be configured to have a secondary preset, three-dimensional shape when in the radially expanded state. In some embodiments, the proximal section can comprise a first bend within a first plane and a second bend out of the first plane.

For example, in some embodiments, the distal section can comprise a first preset bend and a first portion of the distal section, distal to the first preset bend, the first portion extending generally within a first plane. The distal section can also comprise a second bend disposed proximal to the first bend. A second portion of the distal section, proximal to the second bend, can extend in a second plane different from the first plane. The distal section can further comprise a third bend disposed distal to the first bend. A third portion of the distal section, distal to the third bend, can extend in a third plane different from the second plane.

The braid length can be from about 50 mm to about 150 mm. In some embodiments, the braid length can be from about 70 mm to about 130 mm. Further, the braid length can be from about 90 mm to about 100 mm. The braid length can also be about 100 mm.

The coil can be configured to have outer diameter that is substantially constant. Further, the coil length can be from about 20 mm to about 80 mm. In some embodiments, the coil length can be from about 30 mm to about 60 mm. The coil length can also be from about 35 mm to about 50 mm. Further, the coil length can be about 40 mm.

In some embodiments, the first diameter can be substantially the same as the coil diameter when the proximal section is in the delivery lumen. The first diameter can be from about 0.014 inches to about 0.034 inches. The first diameter can be from about 0.016 inches to about 0.027 inches. In some embodiments, the first diameter can be from about 0.017 inches to about 0.021 inches. The second diameter can be from about 2 to about 8 times the first diameter. The second diameter can be from about 2.4 to about 7 times the first diameter. Further, the second diameter can be from about 2.8 to about 5.8 times the first diameter.

In some embodiments, the device can be configured such that a wall of the proximal section comprises a flow diverting pore size. A "flow diverting pore size" can refer to an average pore size of pores (in at least a section of a device) that is sufficiently small enough to interfere with or inhibit fluid exchange through the pores of that section.

A device (e.g., at least a proximal section of the device) can have an active section or a flow diverting section with a flow diverting pore size when the pores of the section are sized to inhibit flow of blood through the sidewall into an aneurysm to a degree sufficient to lead to thrombosis and healing of the aneurysm when the tubular member is positioned in a blood vessel and adjacent to the aneurysm.

For example, a flow diverting pore size can be achieved when pores in the flow diverting or active section have an average pore size of less than about 500 microns when the device (e.g., stent) is in the expanded state. In some embodiments, the average pore size can be less than about 320 microns. Further, the average pore size can be from about 25 microns to about 350 microns. The average pore size can also be from about 40 microns to about 200 microns. Further, in some embodiments, the average pore size can be from about 60 microns to about 150 microns. Furthermore, the average pore size can be about 120 microns.

Average pore sizes that are about within such ranges can operate to divert fluid flow and induce thrombosis within the lumen or interior volume enclosed by the wall. The pores can have a pore size that is generally constant. The pores can have an average pore size that is measured using an inscribed circle diameter.

Additionally, in some embodiments, a device (e.g., stent) can be provided with a porosity in the range of 10%-95% may be employed in the expanded braid to achieve these effects. In some embodiments, a porosity in the range of 30%-90% may be employed to achieve these effects. Further, a porosity in the range of 50%-85% may be employed to achieve these effects.

The system can also comprise a shaping member extending within the proximal section and coupled to the proximal section. The shaping member can comprise thrombogenic fibers. The shaping member can also comprise a helical shape.

For example, the shaping member can be coupled to the proximal and distal ends of the distal section. In the compressed state, the shaping member can define a longitudinal length that is greater than a longitudinal length of the distal section such that when the distal section is in the compressed state. Further, the shaping member can exert an elongating force against the proximal and distal ends of the distal section.

Optionally, the shaping member can be coupled to the proximal and distal ends of the distal section and bias the proximal and distal ends toward each other to assist in expanding the distal section.

The system can also comprise a transition section between the proximal and distal sections. The transition section can have a lower flexibility per unit length than the coil flexibility and the braid flexibility. The transition section can also comprise a tubular or solid member that interconnects the proximal and distal sections.

The proximal section can comprise proximal and distal ends, and the distal end of the distal section can be closed. Further, the proximal end can also be closed.

In some embodiments, the distal section can comprise a filament configured to generate heat when exposed to magnetic resonance imaging for promoting thrombus formation.

In order to facilitate delivery and expansion, the system can further comprise a push wire that is detachably coupled to a proximal end of the occlusive device. Further, the system can comprise a delivery sheath that is configured to house the occlusive device and deliver the occlusive device into the aneurysm. The delivery sheath can be retractable relative to the occlusive device to permit expansion of the occlusive device within the aneurysm.

Some embodiments can also provide methods of treating an aneurysm. For example, the clinician can position a catheter, within a vessel, adjacent the aneurysm. The clinician can then advance, from a distal end of the catheter, a distal section of an occlusive device. The distal section can comprise a coil having a coil length and a coil diameter. The clinician can also expand a proximal section of the device from a radially compressed state with a first diameter when positioned within the delivery lumen to a radially expanded state with a second diameter, greater than the coil diameter, when unconstrained by advancing the proximal section out of the distal end of the catheter.

Further, in some embodiments, as the proximal section is advanced out of the distal end of the catheter, the distal section can distribute, along at least a portion of the coil length, a force of the advancing along an aneurysm interior wall. The proximal section can comprise a flexibility that is greater than a distal section flexibility per unit length.

In some implementations of the method, advancing the distal section can comprise abutting the aneurysm interior wall with a sidewall of the coil.

Further, the method can also comprise advancing an additional occlusive device into the aneurysm. For example, the additional occlusive device can comprise at least one of a non-expanding coil or a braided device. The additional occlusive device can also have a diameter less than the proximal section diameter.

In some implementations, the proximal section of the device can be positioned within the aneurysm such that a segment of the proximal section extends across an ostium of the aneurysm to inhibit egress of the additional device.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

In the following detailed description, numerous specific details are set forth to provide a full understanding of the subject technology. It should be understood that the subject technology may be practiced without some of these specific details. In other instances, well-structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present inventions may be disclosed or shown in the context of aneurysm therapy, such embodiments can be used in other occlusive therapies within the vasculature. Furthermore, various applications of such embodiments and modifications thereto, which may occur to those who are skilled in the art, are also encompassed by the general concepts described herein.

In accordance with an aspect of some embodiments disclosed herein, occlusive devices and methods of use are provided that provide advantages over the use of, for example, only a traditional coil in occluding an aneurysm. Some embodiments can provide a greater volume than traditional coils, which can allow less device material to be deployed while tending to increase the thrombogenicity of the implanted device. Further, some embodiments can also be easier to manipulate within the aneurysm dome or cavity. For example, the device can more easily conform to the interior shape of the aneurysm cavity. Furthermore, when an aneurysm begins to reduce in size, aspects of some embodiments allow the device to be deformable such that the device can be compressed or collapse in size to promote healing of the aneurysm, which is not generally possible using traditional coils or other devices.

Figure 1:
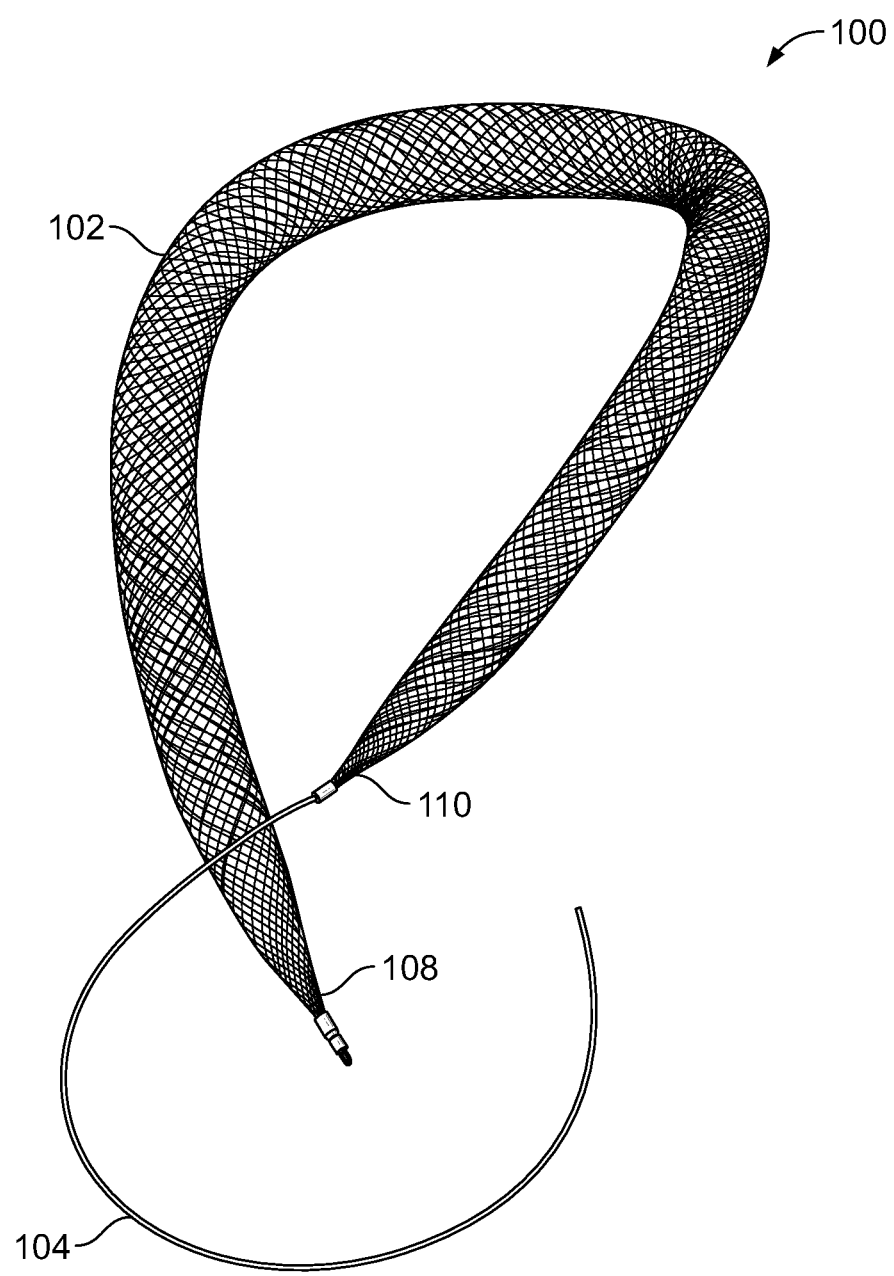
FIG. 1 illustrates an occlusive device in an unconstrained configuration, according to some embodiments.

FIG. 1 depicts one embodiment of an occlusive device 100 that is suitable for occluding body spaces such as aneurysms, including neurovascular or intracranial aneurysms, or blood vessels or other hollow anatomical structures. The depicted occlusive device 100 includes a proximal section 102 which can comprise an expandable, generally tubular braid. The proximal section 102 can be self-expanding such that it tends to assume its expanded state in the absence of a constraint. The occlusive device 100 further comprises a distal section 104 coupled to a distal end 110 of the proximal section 102. The depicted distal section 104 is an atraumatic tip coil that extends distally from the distal end 110 of the proximal section 102. Other suitable atraumatic tip structures (e.g., a soft distally extending polymeric member) may used in place of the depicted tip coil.

The proximal section 102 can comprise a braid having a number of strands, such as metallic wires or polymeric filaments, that are braided together to form a tube whose sidewall is formed of the braided wires. A lumen extends along and within the proximal section 102, surrounded by the sidewall. In the proximal section 102 depicted in FIG. 1, both proximal and distal ends 108, 110 are closed. However, one or both of the proximal or distal ends 108, 110 may be open. Closed ends may be formed by crimping, soldering, etc. and other fasteners or methods.

In the occlusive device 100 shown in FIG. 1, the braid of the proximal section 102 assumes a "three-dimensional" configuration in its unconstrained state (or in its semi-constrained state, such as within an aneurysm). One example of this three-dimensional configuration is shown in FIG. 1. This configuration is three dimensional in that the central axis or longitudinal axis of the proximal section 102 does not lie substantially flat, or substantially in a single plane. Instead, the proximal section 102 forms a first curve or bend 200 centered approximately at the longitudinal midpoint of the proximal section 102 (see FIG. 1, and FIG. 2D). This first curve 200 can be characterized by a portion of the proximal section 102 in which a central axis of the proximal section 102 resides substantially within a first plane. At the opposing ends of the first curve 200, the proximal and distal end portions of the proximal section 102 can bend and extend out of the first plane to form second and third bends or curves 202, 204 located proximal and distal, respectively, of the first curve 200. The second and third curves 202, 204 can extend in approximately the same direction away from the plane of the first curve 200, or in opposing directions or otherwise different directions.

Figure 2A:
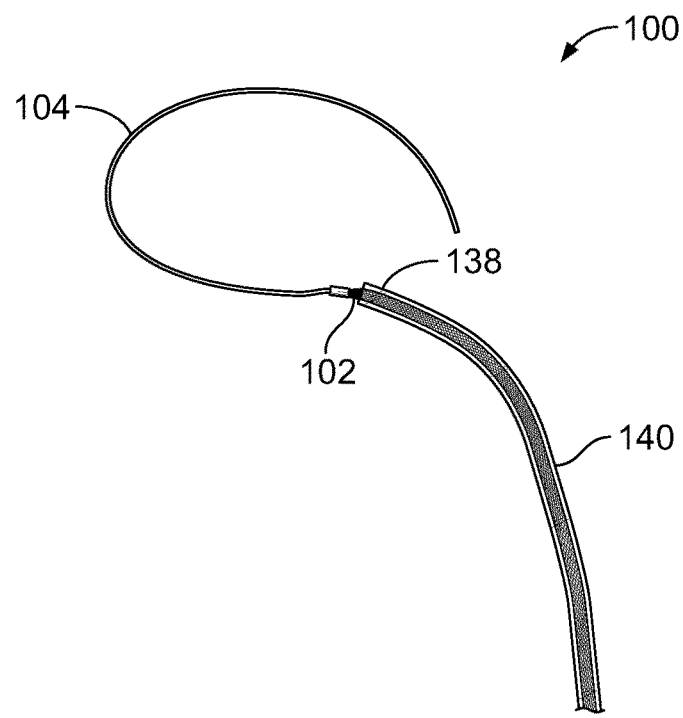
FIG. 2A illustrates the occlusive device of FIG. 1 being urged out the distal end of a catheter, with the tip coil assuming an unconstrained configuration, according to some embodiments.
Figure 2B:
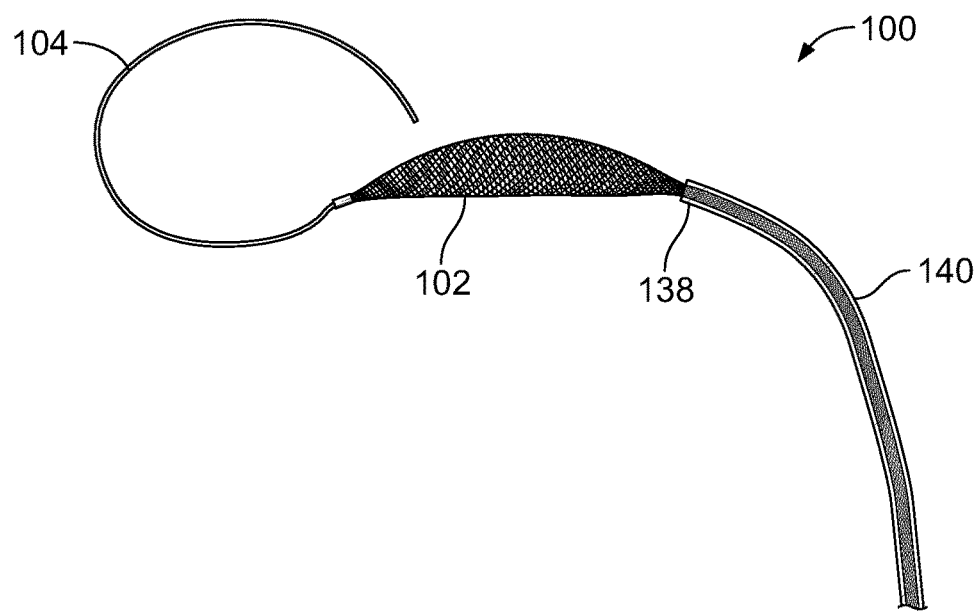
FIG. 2B illustrates the occlusive device being urged out the distal end of a catheter, with the tip coil assuming an unconstrained configuration and the braid beginning to emerge and expand in diameter, according to some embodiments.
Figure 2C:
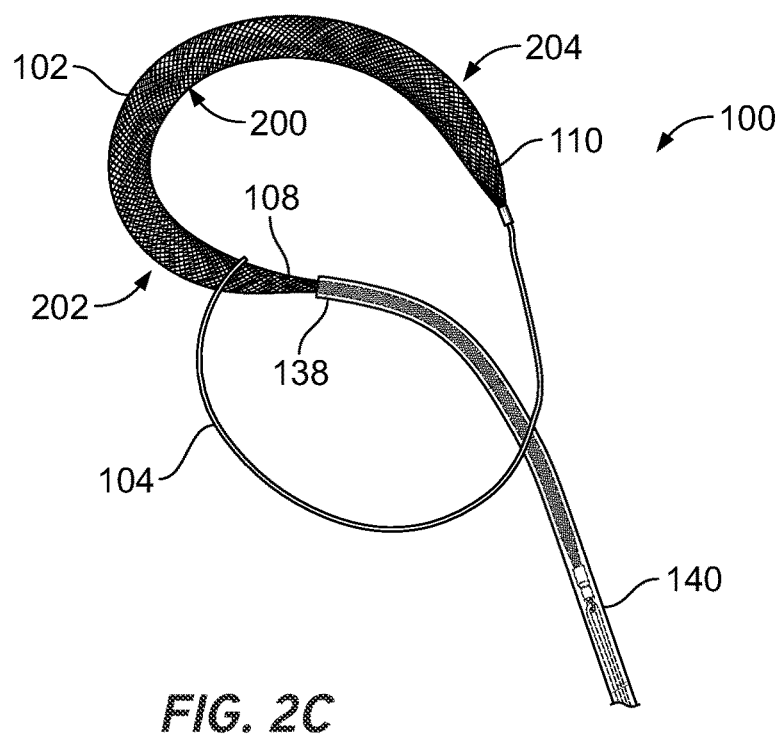
FIG. 2C illustrates the occlusive device being urged out the distal end of a catheter, with the tip coil assuming an unconstrained configuration and the braid beginning to take on an expanded-diameter, three-dimensional unconstrained configuration, according to some embodiments.
Figure 2D:
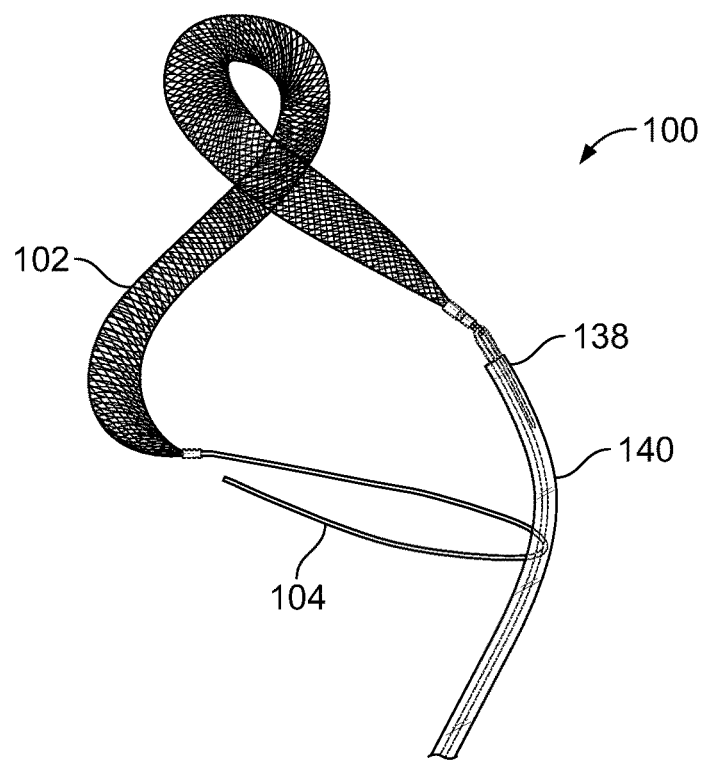
FIG. 2D illustrates the occlusive device completely emerged from the catheter, with the braid in an expanded-diameter, three-dimensional unconstrained configuration, according to some embodiments.

The three-dimensional configuration shown in FIGS. 1 and 2D can be considered a compound curve or multi-planar curve which is one type of three-dimensional configuration that may be employed in the proximal section 102. A spherical three-dimensional configuration can be achieved by winding the proximal section 102 onto a spherical mandrel and heat-setting the proximal section 102. A helix is another type of three-dimensional configuration that may be employed, and implemented by heat-setting the proximal section 102 while wound onto a cylindrical mandrel.

As mentioned previously, the proximal section 102 can comprise an expandable braid, e.g., a self-expandable braid, such that the proximal section 102 can take on a larger diameter along some or all of its length when expanded. Accordingly, when released from a constraint, such as when pushed out of a distal end 138 of a delivery catheter 140, the proximal section 102 can assume a deployed configuration in which the proximal section 102 has both expanded in diameter and taken on a three-dimensional configuration.

In certain embodiments in which the proximal section 102 comprises a braid, which may be useful for use in neurovascular aneurysms, the braid can have a diameter in its expanded state of about 1.5-2.5 mm. The coil or distal section 104 can be configured to have outer diameter that is substantially constant, and can be from about 0.20 mm to about 3 mm, from about 0.30 mm to about 2.5 mm, from about 0.50 mm to about 2 mm, or from about 0.40 mm to about 1.5 mm, and in some embodiments, about 0.45 mm.

Further, in some embodiments, the collapsed diameter of the proximal section 102 can be substantially the same as the coil or distal section diameter when the proximal section is in the delivery lumen. The collapsed diameter can be from about 0.014 inches to about 0.034 inches. The collapsed diameter can be from about 0.016 inches to about 0.027 inches. In some embodiments, the collapsed diameter can be from about 0.017 inches to about 0.021 inches (which can facilitate delivery through catheters of similar size). The expanded diameter can be from about 2 to about 8 times the collapsed diameter. The expanded diameter can be from about 2.4 to about 7 times the collapsed diameter. Further, the expanded diameter can be from about 2.8 to about 5.8 times the collapsed diameter.

However, other diameters are within the scope of the present disclosure. For example, the braid could be sized with a diameter that is about one-third to one-half the diameter or maximum width of the aneurysm into which the occlusive device 100 is to be placed. Such a braid should preferably be shorter than a small-diameter braid to be used for a similar application.

Further, the coil or distal section length can be from about 20 mm to about 80 mm. In some embodiments, the coil length can be from about 30 mm to about 60 mm. The coil length can also be from about 35 mm to about 50 mm. Further, the coil length can be about 40 mm. The braid may have the capability of foreshortening when expanding from its compressed length (and also lengthening when being compressed from its expanded form).

Occlusive devices to be used in the above-mentioned neurovascular aneurysms may have braid or proximal sections that are about 40-180 mm long when in the expanded state. The braid or proximal length can be from about 50 mm to about 150 mm. In some embodiments, the braid length can be from about 70 mm to about 130 mm. Further, the braid length can be from about 90 mm to about 100 mm. In some embodiments, the braid length can also be about 100 mm.

The proximal section 102 can be configured to have embolic properties so as to interfere with blood flow in the body space (e.g., aneurysm) in which the occlusive device 100 is deployed. The porosity and/or average pore size of the (expanded) proximal section 102 can be selected to interfere with blood flow to a degree sufficient to thrombose the aneurysm or other body space.

In some embodiments, to interfere with blood flow to a degree sufficient to thrombose the aneurysm or other body space, the pores can have an average pore size that is less than or equal to about 500 microns. The pores can have an average pore size that is less than or equal to about 320 microns. The pores can have an average pore size that is from about 50 microns to about 320 microns. The pores can have a pore size that is generally constant. The pores can have an average pore size that is measured using an inscribed circle diameter.

For example, a porosity in the range of 10%-90% and/or average pore size in the range of 25-250 microns (inscribed diameter) may be employed in the expanded proximal section 102 to interfere with blood flow to a degree sufficient to thrombose the aneurysm or other body space.

As mentioned previously, the proximal section 102 can comprise a braid that can be constructed from metal wires or strands. Suitable metals include stainless steel (e.g., 304V stainless steel), alloys of cobalt-nickel, cobalt-chromium or cobalt-chromium-nickel (e.g., L605 cobalt-chromium-nickel, 35NLT cobalt-chromium-nickel, or MP35N cobalt-chromium-nickel), nitinol, platinum or platinum-tungsten. Biodegradable wires may be employed, formed from magnesium or its alloys, iron or ferric alloys, or polymers such as PLA or PGA. The braid may be formed from combinations of the above-specified wires, for example using a group of cobalt-alloy wires braided with a group of platinum-tungsten wires. In some embodiments, the braid wires can be about 0.0010 inches in diameter, or in the range of 0.0008 to 0.0020 inches in diameter. A number of different braid patterns may be employed, but one possible pattern employs 32 strands braided in a one-over-two-under-two arrangement, at 120 picks per inch. In one embodiment, the braid is constructed entirely of 304V stainless steel strands. In another embodiment, a combination of L605, nitinol and platinum-tungsten wires are employed.

The braid wires can be monofilaments, cables, wrapped wires or the like. One or more of the braid wires can comprise hypotubes, which can include micropores formed in the sidewalls thereof. An absorbable and/or thrombogenic material (including any such materials discussed herein) can be positioned in the lumen of the hypotubes and exposed to contact with ambient blood and anatomy via the micropores.

One or more of the braid filament materials can be selected to generate heat when exposed to magnetic resonance imaging. For example, iron or martensitic stainless steel wires may be employed in the braid. With such a braid, the treated body space or aneurysm holding the occlusive device 100 may be exposed to MRI following implantation. The braid generates heat in response to the MRI, which in turn promotes formation of thrombus in the aneurysm or body space.

The lumen of the proximal section 102 may be empty or void, as shown in the depicted examples. This provides the proximal section 102 with great freedom to expand, contract, shorten or lengthen during use. Alternatively, material may be located in the lumen, such as thrombogenic fibers (e.g., polymeric and/or absorbable fibers such as PLA or PGA fibers which can be crimped or bulked) or metallic elements like coils or a core wire. A core coil may be employed, such as a platinum wire having a primary wind and extending generally along the central axis of the proximal section 102 from end to end thereof.

The distal section 104 can comprise a soft or atraumatic tip coil that extends generally distally from the distal end 110 of the proximal section 102. For example, the distal section 104 can be a flexible platinum-tungsten coil having a primary wind oriented generally about the longitudinal axis of the occlusive device 100. The distal section 104 can include a core wire or the like extending longitudinally therein to function as an anti-elongation device. The distal section 104 can have a two-dimensional configuration in its unconstrained (or semi-constrained) state, such as the two-dimensional curved configuration shown in FIGS. 1 and 2A-2D. Alternatively, the distal section 104 can have a three-dimensional configuration when in the unconstrained/semi-constrained state.

Figure 3A:
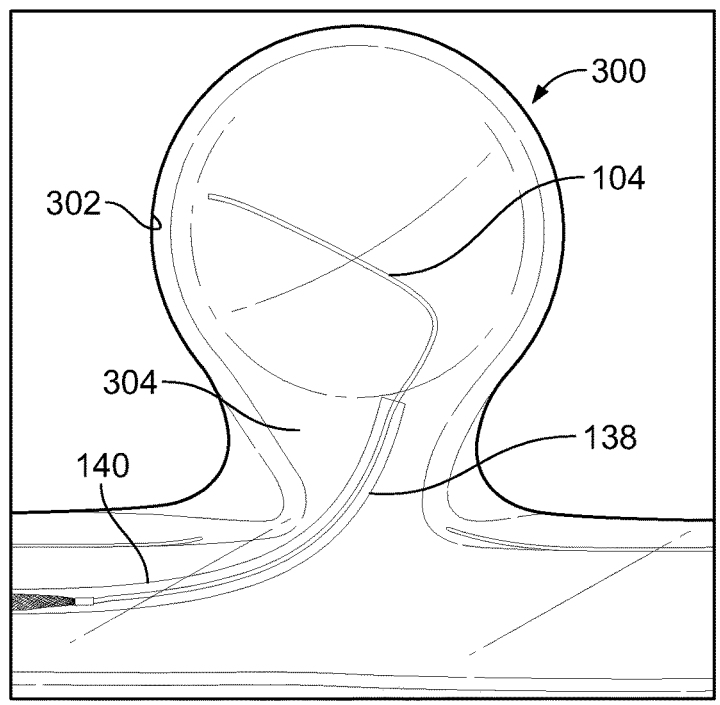
FIG. 3A illustrates the occlusive device of FIG. 1 being urged out the distal end of a catheter and into an aneurysm, with the tip coil assuming an unconstrained or semi-constrained configuration, according to some embodiments.

The distal section 104 can act as a flexible, atraumatic lead-in for the occlusive device 100 when inserting the device in a body space such as an aneurysm. As seen in FIG. 3A, as the device is delivered from a catheter 140 into an aneurysm, the distal section 104 emerges first. Because of the relative softness of the distal section 104, the trauma experienced by the aneurysm is minimized. The distal section 104 begins to take on its curved, semi-constrained configuration (FIG. 3B), forming a curve with a diameter somewhat smaller than that of the aneurysm. The deployed distal section 104 then functions as a guide that prevents the oncoming proximal section 102 from impacting the aneurysm wall "head-on," making contact with a single point or concentrated area, such as can be done with a sharp, pointed, stiff, and/or hard tip or point of contact. The proximal section 102 can then advance into the aneurysm without undue chance of injury to the aneurysm wall.

One embodiment of a method of treating an aneurysm 300 with the occlusive device 100 proceeds as follows. First, a catheter 140 (such as a microcatheter) is advanced within the parent vessel to a location at or near the aneurysm 300. The occlusive device 100 is advanced distally within the catheter lumen (e.g., via a push wire removably coupled to the proximal end 108 of the proximal section 102), with the distal section 104 leading the proximal section 102 such that the distal section 104 emerges from the distal end 138 of the catheter 140 and enters the aneurysm 300 first (FIG. 3A).

Figure 3B:
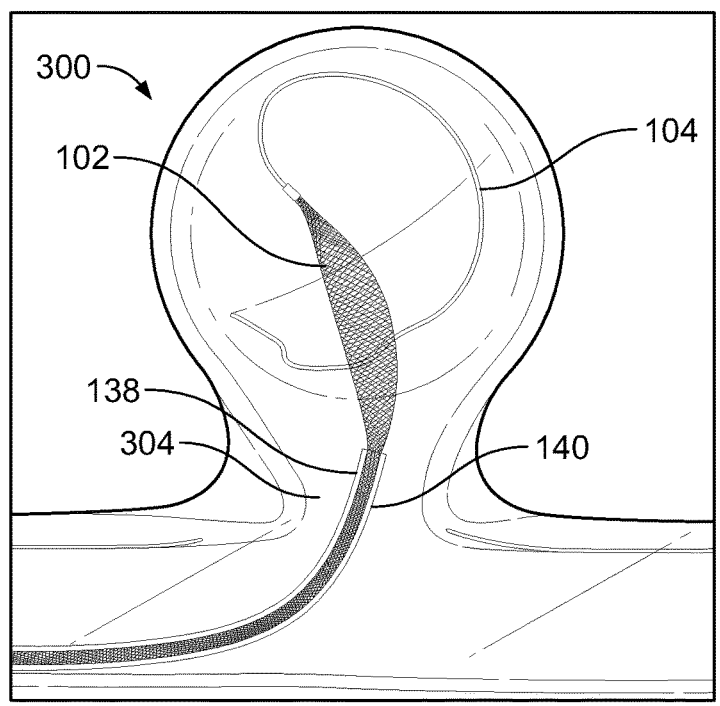
FIG. 3B illustrates the occlusive device being urged out the distal end of a catheter and into an aneurysm, with the tip coil assuming an unconstrained or semi-constrained configuration and the braid beginning to emerge and expand in diameter, according to some embodiments.
Figure 3C:
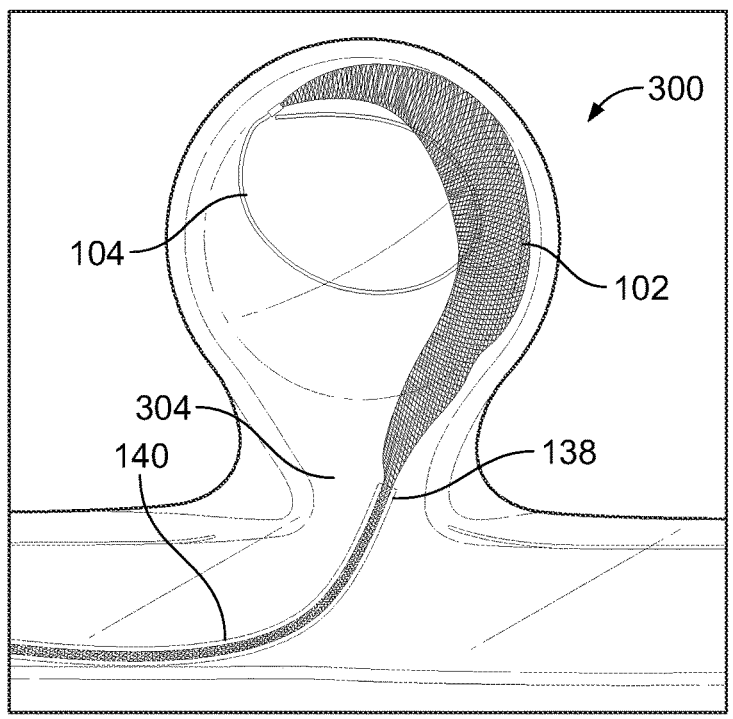
FIG. 3C illustrates the occlusive device being urged out the distal end of a catheter and into an aneurysm, with the tip coil assuming an unconstrained or semi-constrained configuration and the braid continuing to emerge and expand in diameter, according to some embodiments.
Figure 3D:
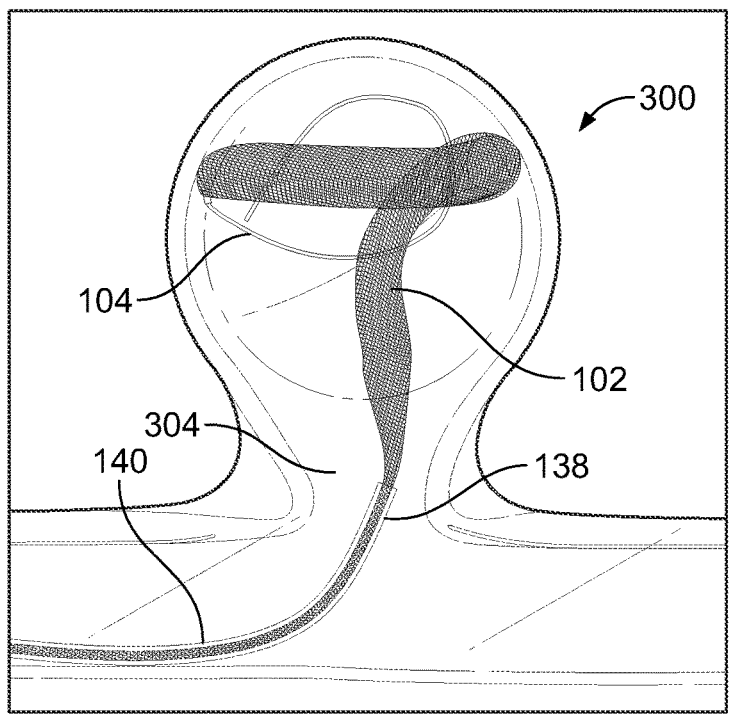
FIG. 3D illustrates the occlusive device being urged out the distal end of a catheter and into an aneurysm, with the tip coil assuming an unconstrained or semi-constrained configuration and the braid beginning to take on an expanded-diameter, three-dimensional unconstrained configuration, according to some embodiments.
Figure 3E:
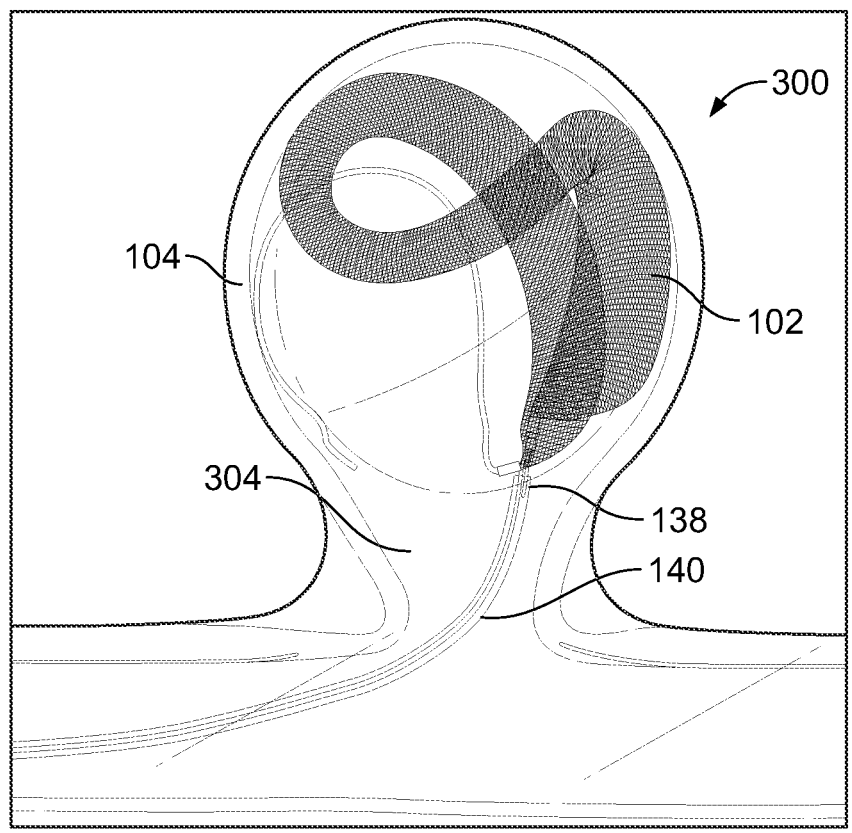
FIG. 3E illustrates the occlusive device nearly completely deployed from the distal end of a catheter and into an aneurysm, with the tip coil assuming an unconstrained or unconstrained configuration and the braid in an expanded-diameter, three-dimensional unconstrained configuration, according to some embodiments.
Figure 4:
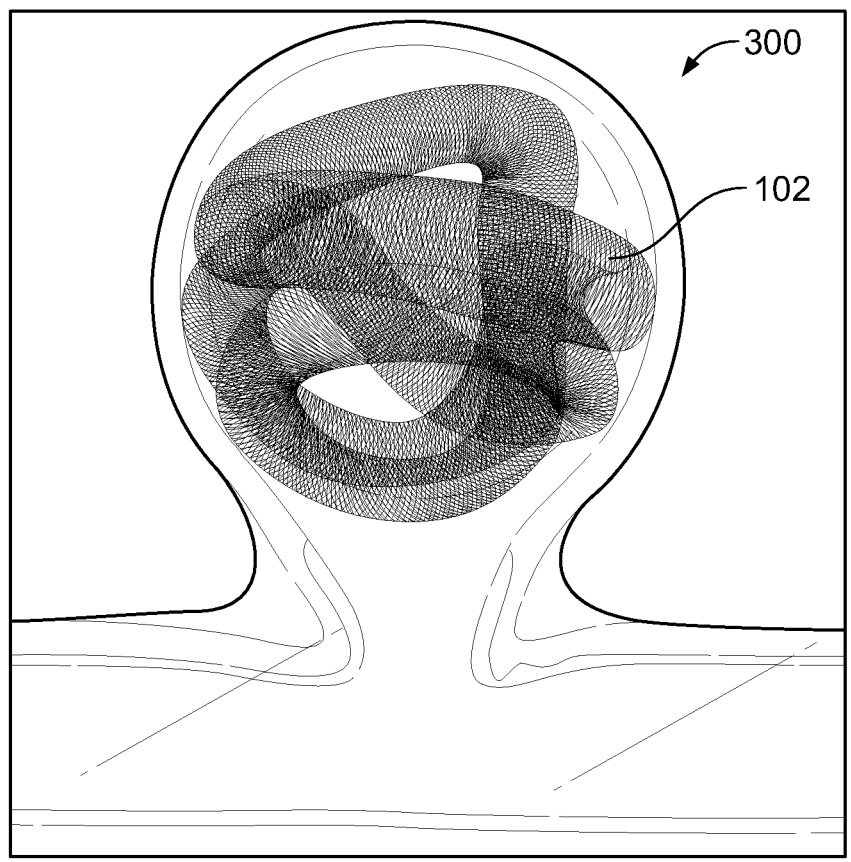
FIG. 4 depicts an embodiment of the occlusive device that lacks a tip coil, positioned in an aneurysm, according to some embodiments.

As it enters the aneurysm 300, the distal section 104 can be caused to take on its unconstrained or semi-constrained configuration such as the two-dimensional curved configuration shown in FIGS. 3A-3B. The proximal section 102 is then advanced out of the distal end 138 of the catheter 140 and into the aneurysm 300. As the proximal section 102 expands during advancement out of the distal end 138 of the catheter 140, the distal section 104 can be configured to distribute, along at least a portion of the coil length, a force of the advancement along an aneurysm interior wall 302.

The proximal section 102 can thus allowed to expand in diameter (and in some embodiments to shorten as well) and take on an unconstrained or semi-constrained configuration, which can be a three-dimensional configuration such as any of those discussed herein. When the occlusive device 100 is fully deployed in the aneurysm 300, its expanded-diameter, three-dimensional configuration interferes with blood flow in the aneurysm 300, leading to thrombosis. Thus the occlusive device 100 thromboses the aneurysm 300 and seals it off from exposure to blood flow, reducing or eliminating the risk of rupture and hemorrhage.

In further embodiments of this method, the aneurysm 300 is a ruptured, wide-neck, large or giant aneurysm. Where the aneurysm 300 is ruptured and/or has a wide neck 304, the method further comprises preventing the occlusive device 100 from passing through the rupture or the neck 304 by allowing or causing the proximal section 102 to expand in diameter, and/or assume a three dimensional configuration.

The method can further comprise employing the deployed occlusive device 100 as a framing or filling device and delivering additional occlusive devices into the aneurysm 300, which devices can have proximal sections of the expanding-braid type depicted herein, or standard non-expanding coils. The device 100 can span the neck 304 in order to prevent herniation of itself, and if other devices are also implanted into the aneurysm, the other devices as well.

Figure 5A:
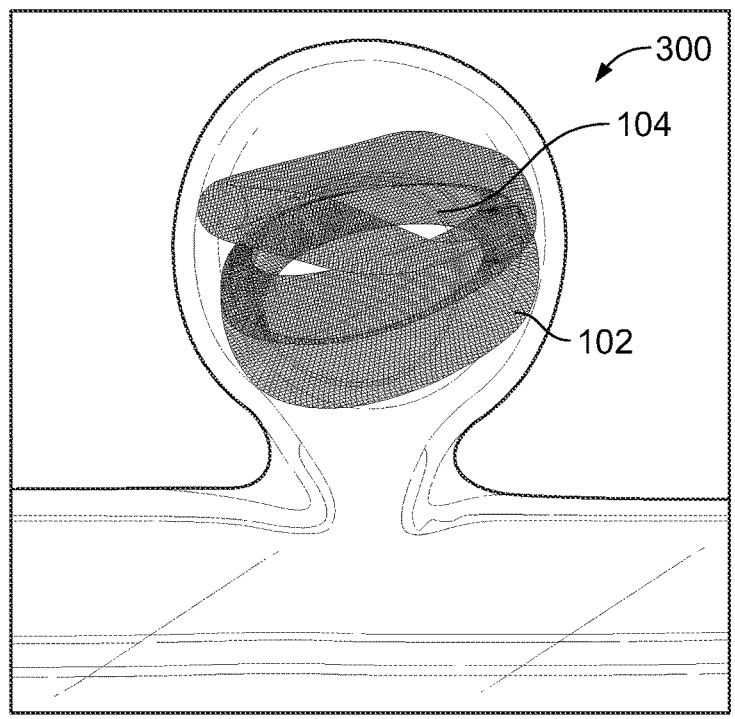
FIGS. 5A, 5B and 5C are several views of another embodiment of the occlusive device with a braid and tip coil, positioned in an aneurysm, according to some embodiments.
Figure 5B:
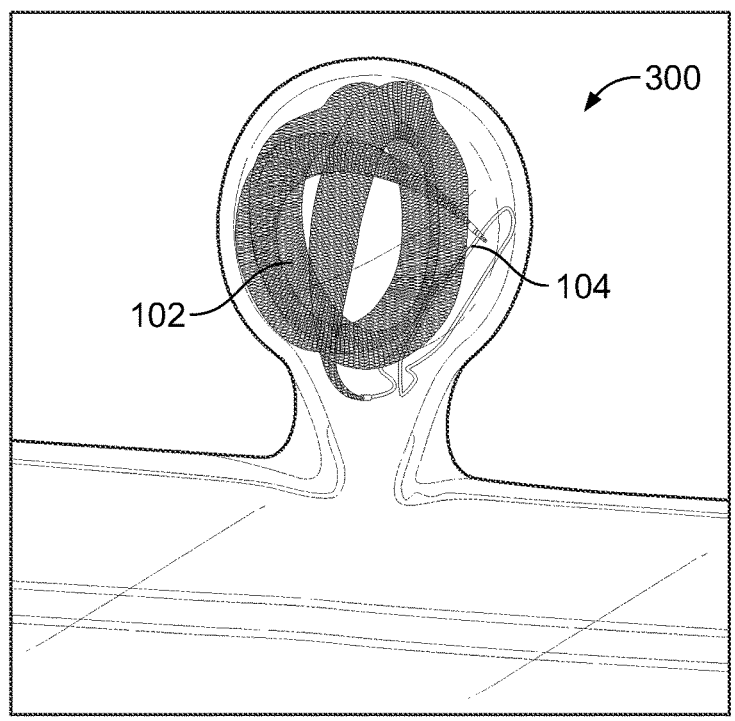
Figure 5C:
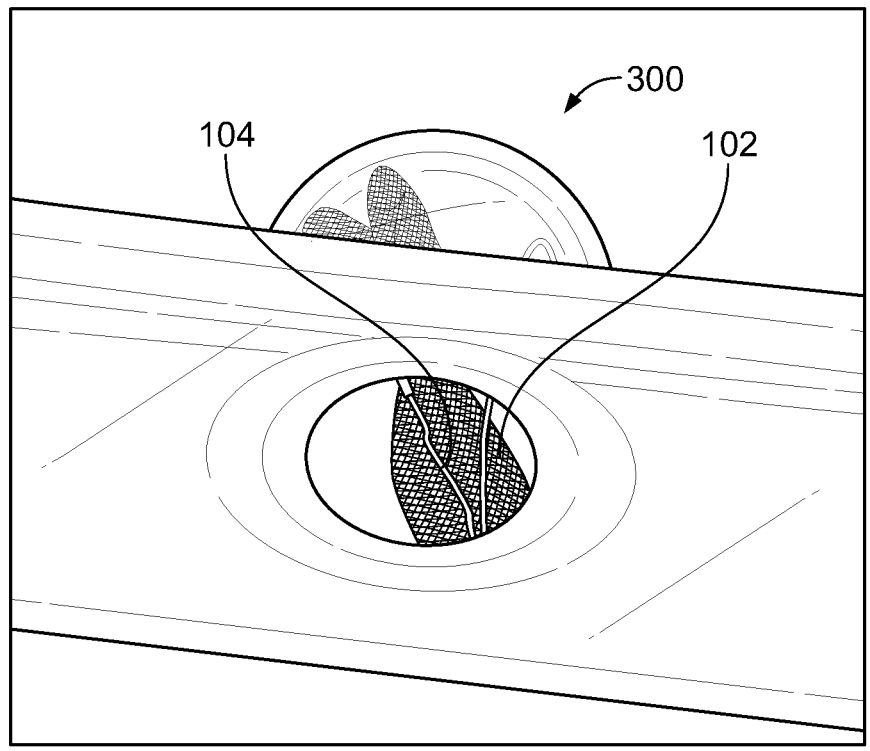
Figure 6A:
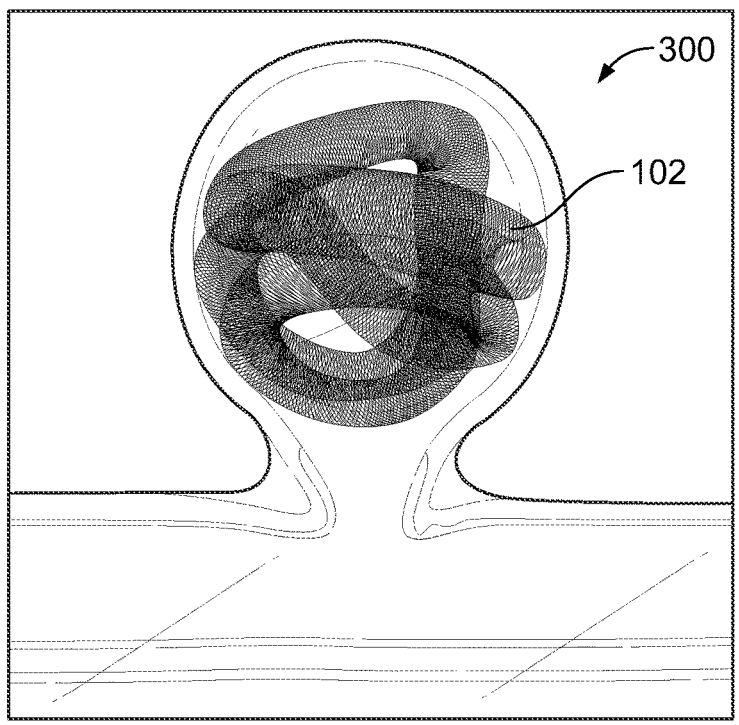
FIGS. 6A, 6B and 6C are several views of another embodiment of the occlusive device with a braid and no tip coil, positioned in an aneurysm, according to some embodiments.
Figure 6B:
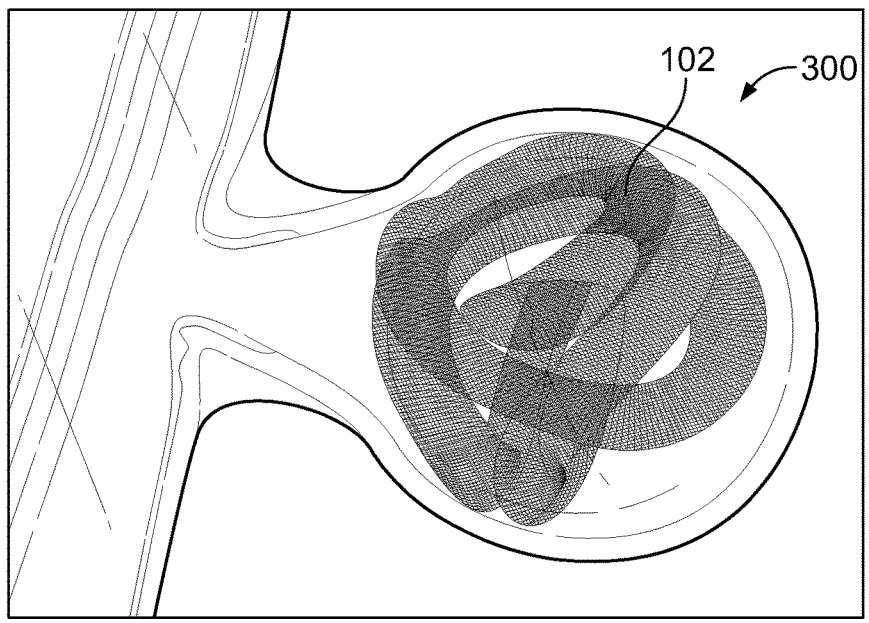
Figure 6C:
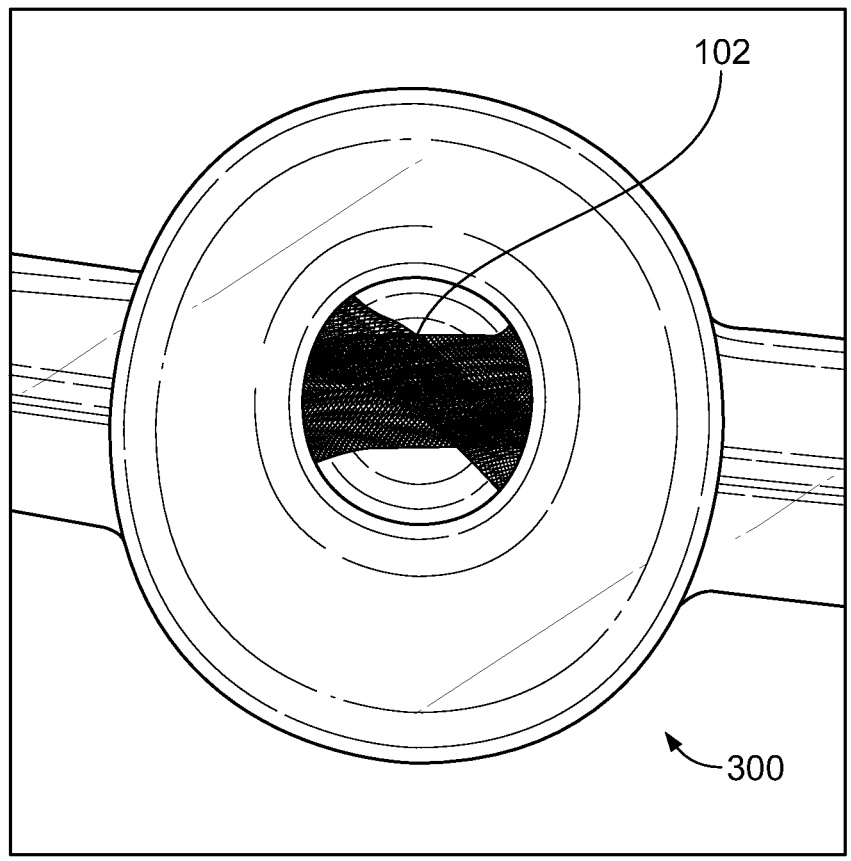

Additionally, the occlusive device can advantageously provide multiple crossing points and a greater device surface area spanning the neck 304 than other devices. As generally shown in FIGS. 5C and 6C, when the device 304 is expanded within the aneurysm 300, the proximal section 102 can overlap with itself and the distal section 104 to create multiple crossing points and fewer and smaller gaps than otherwise possible using than traditional coils, baskets, or other devices. Additionally, because the proximal portion 102 comprises an internal volume or lumen that is greater in size than a lumen of traditional coils while being much smaller than a diameter of the aneurysm 300, the overlapping and turning of the proximal portion 102 within the aneurysm 300 and across the neck 304 can create much smaller pockets or volumes separated by flow diverting layers that can promote clotting at a much higher rate than traditional coils, baskets, or other devices, as well as promoting endothelialization across the neck 304 than traditional coils, baskets, or other devices.

The method can further comprise preventing the occlusive device 100 from passing through the aneurysm neck 304 by allowing or causing the proximal section 102 to expand in diameter, and/or assume a three dimensional configuration.

Where employed, the push wire can include a distal hook that is looped through an eyelet formed at the proximal end of the occlusive device 100. Other attachments can be employed, including those with a mechanical or electrolytic detachment capability. As an alternative means of delivery, the occlusive device 100 can be loaded into the distal portion of the lumen of a delivery sheath, which in turn can be configured to be delivered to the treatment site through a larger catheter. The delivery sheath, with the preloaded occlusive device 100, is advanced through the catheter 140 to the treatment site and the occlusive device 100 can be deployed from the distal end of the delivery sheath via a pushwire or pushrod.

Figure 7:
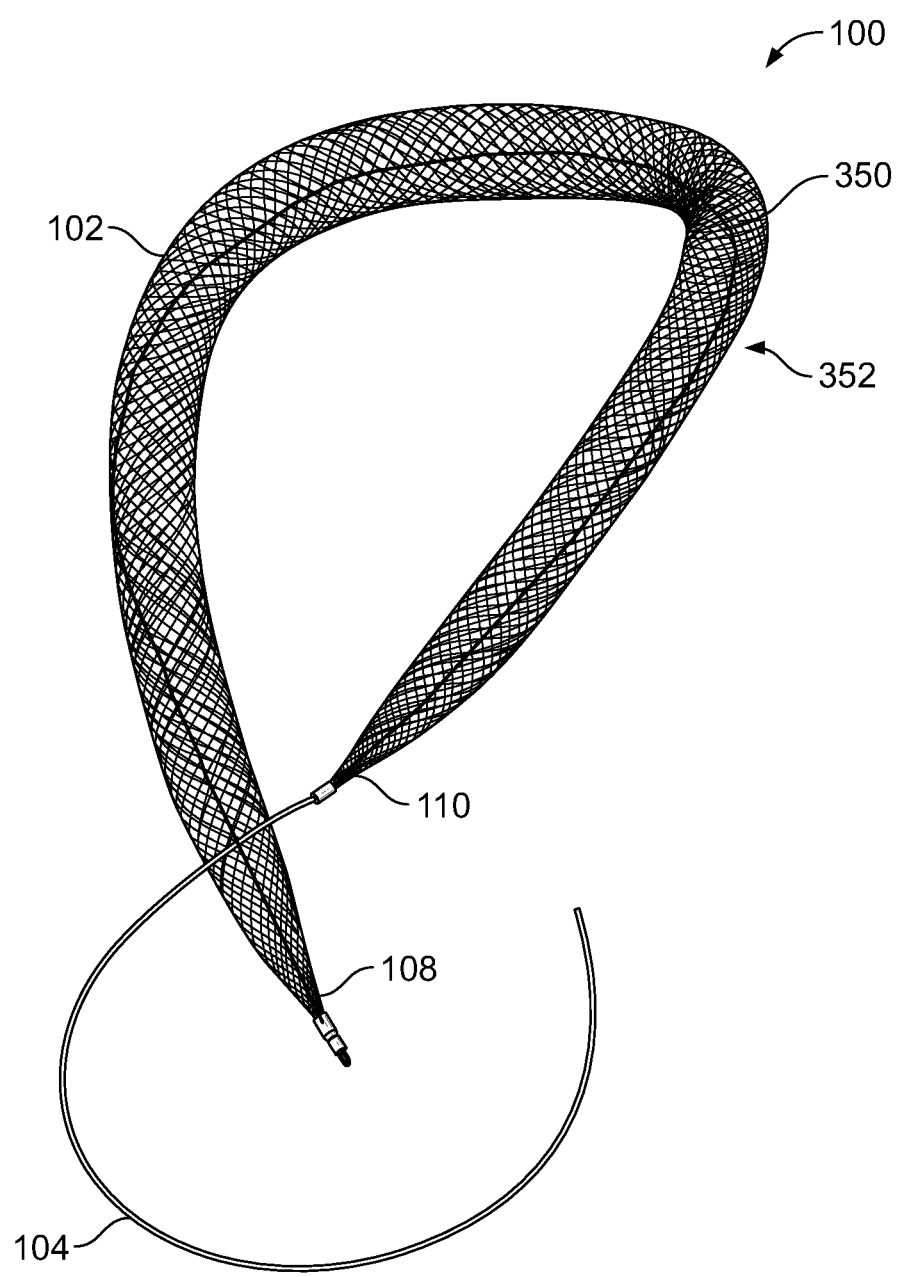
FIG. 7 is an occlusive device, according to some embodiments.

As illustrated in FIG. 7, in further embodiments of the occlusive device 100, an internal member 350 may be disposed in the lumen of the proximal section 102, extending generally longitudinally along the lumen. The internal member 350 can optionally extend from a proximal end 108 of the proximal section 102 to the distal end 110 thereof. As shown in FIG. 7, the internal member 350 can optionally comprise a shaping member, various embodiments of which are discussed in further detail herein. A shaping member 350 (or other form of internal member) can comprise an elongate monofilament, such as a single-strand metallic wire or polymeric filament, or a multifilament such as a cable formed from wires and/or filaments of single or multiple materials twisted together, or an elongate braid or woven structure, or a bundle of multiple generally parallel filaments held together with hoops or other suitable bundling structure.

A shaping member 350 may be employed in the lumen of the proximal section 102 to impart a two- or three-dimensional configuration to the proximal section 102 when a shaping member assembly 352 (e.g., the proximal section 102) is in its unconstrained state. The shaping member 350 may be employed to impart any of the two- or three-dimensional configurations discussed herein, or other suitable such configurations. The desired unconstrained configuration can be heat-set or otherwise processed into the shaping member 350. The shaping member 350 can be employed with a proximal section which itself has no particular heat-set or otherwise pre-set unconstrained configuration, or with a proximal section which does have a two- or three-dimensional unconstrained configuration. Where only the shaping member 350 has a pre-set unconstrained configuration, the shaping member 350 can urge the proximal section into a two- or three-dimensional unconstrained or semi-constrained configuration upon release from a delivery catheter 140 or into an aneurysm 300. The unconstrained configuration thus achieved by the proximal section 102 can be generally similar to the unconstrained configuration that is pre-set in the shaping member 350.

Instead of or in addition to a two or three-dimensional configuration as discussed above, the internal member or shaping member 350 can be generally helical, wherein the shaping member 350 is coiled generally about the central axis of the proximal section 102, and the radially outer surface of the shaping member 350 abuts or approaches the inner surface of the proximal section 102. Such a shaping member 350 can be configured to self-expand to a larger-diameter configuration within the lumen of the proximal section 102, and thereby act as an expansion assist for the proximal section 102, tending to urge the proximal section 102 open towards a larger-diameter configuration when the shaping member assembly 352 is released from constraint, e.g., from within a delivery catheter 140.

Such a shaping member 350 can also take on a reduced-diameter and/or substantially straight configuration when the shaping member assembly 352 is radially compressed such as within the lumen of a delivery catheter 140. This may be considered a delivery configuration of the proximal section 102 or shaping member assembly 352. In this delivery configuration, the reduced-diameter and/or substantially straight shaping member 350 can serve as a delivery assist by imparting column strength to the proximal section 102. Where such a helical shaping member is employed, the proximal and distal ends of the shaping member can be securely coupled to the proximal and distal ends 108, 110, respectively, of the proximal section 102 and the longitudinal contraction/elongation properties of the proximal section 102 and shaping member can be matched so that one of the expanding or contracting proximal section 102 or shaping member does not tend to overstretch or buckle the other.

In another implementation, a generally helical internal member or shaping member can be employed and coupled to both ends 108, 110 of the proximal section 102 as discussed above. However, the internal member 350 can be configured to elongate at a somewhat higher rate than the proximal section 102 when radially constrained, such that insertion of the shaping member assembly into a delivery catheter 140 lumen elongates the shaping member, which in turn forces the proximal section 102 into an elongated, radially contracted configuration which is more elongated and radially contracted than it would attain without the force of the shaping member. The shaping member therefore holds the proximal section 102 in a radially contracted state during delivery. This reduces the friction between the proximal section 102 and catheter 140 and makes delivery of the occlusive device 100 easier.

Instead of or in addition to elongation as discussed herein, the proximal section 102 can be pretwisted to provide a lower profile for delivery.

Where an internal member or shaping member 350 of relatively high column strength is employed, and a distal end or portion of the shaping member 350 is securely coupled to a distal end 110 or portion of the proximal section 102, the shaping member 350 may be used to urge the proximal section 102 into a reduced diameter configuration by applying a distally-directed longitudinal force to the distal end 110 or portion of the proximal section 102. This may be done, for example, while the shaping member assembly 352 is positioned in the lumen of a delivery catheter 140, and by manually pushing a proximally extending portion of the internal member or shaping member 350 in a distal direction. This in turn elongates the proximal section 102 while reducing its diameter within the catheter 140, easing passage of the proximal section 102 through the catheter 140.

The internal member or shaping member 350 may comprise one or more nitinol wires, which can be pre-shaped as discussed above. One suitable form of nitinol is martensitic nitinol, which can be used to provide a relatively internal member or shaping member 350. In addition, a nitinol or martensitic nitinol (or other material) shaping member can be employed which is substantially straight (and relatively elongated) while at or near room temperature, and coiled (and relatively shortened) while at or near human body temperature. Such a shaping member can be used as discussed above to hold the proximal section 102 in a radially contracted state during delivery through a catheter lumen.

The internal member or shaping member 350 may comprise a wire, cable, braid or the like with one or more relatively soft (e.g., polymeric or elastomeric) pads mounted thereon. Accordingly, when the proximal section 102 of the occlusive device 100 is within the lumen of a catheter 140, the internal member 350 will assume a relatively straight, longitudinally oriented configuration and the proximal section 102 will assume a radially compressed configuration, with its inner wall in contact with one or more of the pads. The proximal section 102 is accordingly gripped between the pads (which are sized to facilitate such gripping) and the inner wall of the catheter 140, and the internal member 350 is accordingly configured to serve as a column or longitudinal force transmission member, such that the occlusive device 100 can be pushed distally along the catheter lumen during delivery by applying a distally-directed force to the occlusive device 100, e.g., at the proximal end 108 of the proximal section 102. The distal force is transmitted along the internal member 350 to the pads, and from the pads to the proximal section 102, which advances distally. The inner wall of the catheter 140 helps to develop sufficient friction between the proximal section 102 and pads to enable force transmission from the pads to the proximal section 102. Where pads of this type are employed on the internal member or shaping member 350, the internal member 350 can be configured to coil into a helix, or assume some other two- or three-dimensional shape, when unconstrained or semi-constrained and thereby cause the pads to disengage from contact with the inner wall of the proximal section 102.

Figure 8:
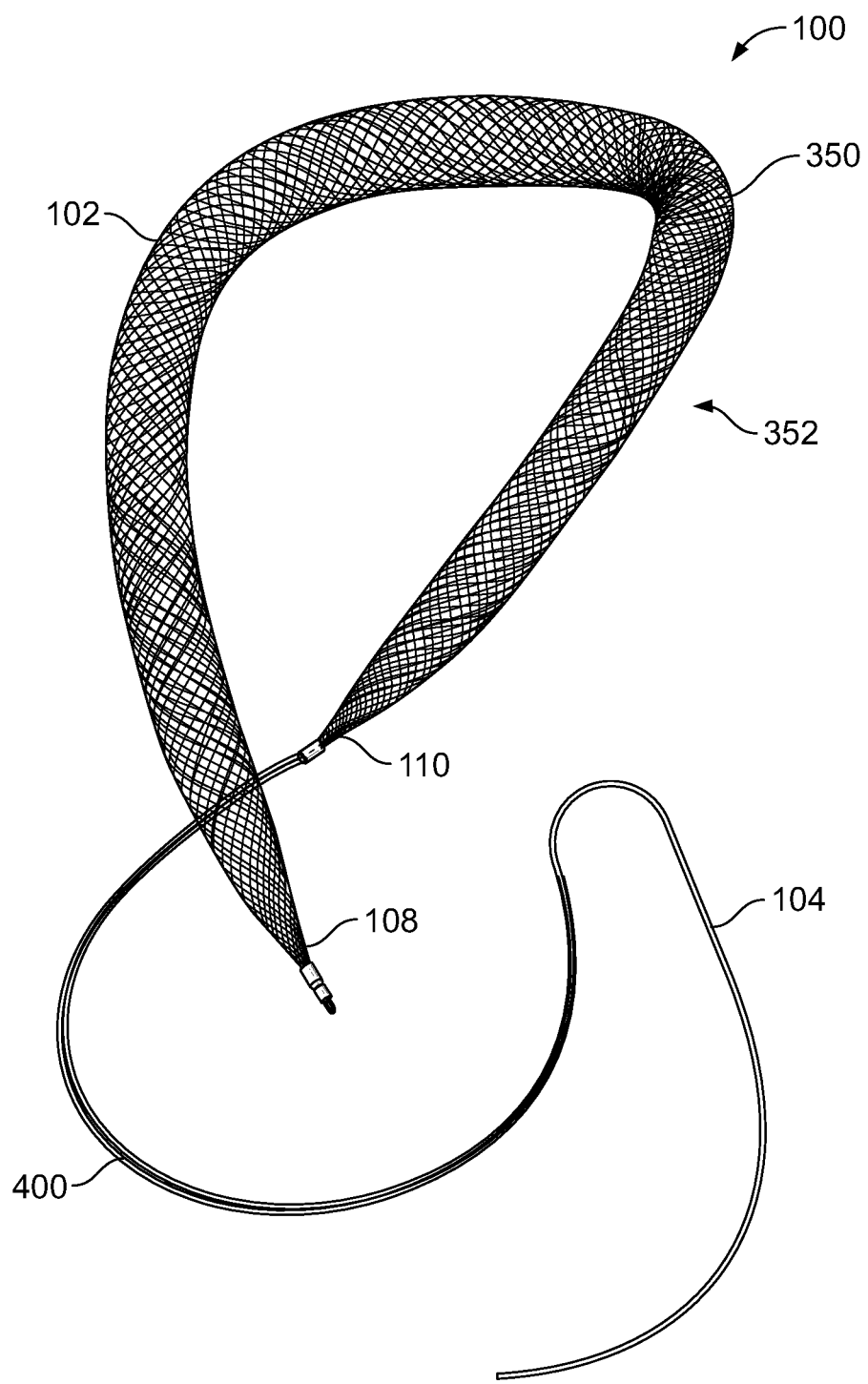
FIG. 8 is another occlusive device, according to some embodiments.

As illustrated in FIG. 8, the device 100 can also comprise at least one transition section 400 between the proximal and distal sections 102, 104. The transition section 400 can have a lower flexibility per unit length than the coil flexibility and the braid flexibility.

In measuring the flexibility for any of the proximal, transition, or distal sections, the flexibility can be determined as a measurement of bending strength per unit length, bending strength for the overall length, yield strength of the section per unit length, or the yield strength of the total length of the section. For example, the bending strength can be calculated using the traditional formula of: $\sigma=(3PL)/(2wt^2)$, where P is the normal force, L is the beam length, w is the beam width, t is the beam thickness, and y is the deflection at load point. Further, the yield strength can be determined experimentally using various specimens and tables to calculate the general yield strength of the sections, including use of the traditional formula of:

$$\sigma = E^*\epsilon.$$

The transition section 400 can also comprise a tubular or solid member that interconnects the proximal and distal sections 102, 104. The transition section 400 can comprise one or more tapered members. In some embodiments, the device 100 can comprise multiple transition sections between the proximal and distal sections 102, 104.

In some embodiments, the transition section 400 can define a length that is greater than or equal to the length of the distal section 104. Further, the length of the proximal section 102 can also be greater than or equal to the length of the distal section 104. Thus, in a mathematical relationship, the ratio of the lengths of the distal section 104 to the transition zone 400 to the proximal section 102 can be expressed as: $1: \geq 1: \geq 1$.

Accordingly, the transition zone 400 can define a length greater than the length of the distal section 104. Further, the transition length can be from about 30 mm to about 120 mm. In some embodiments, the transition length can be from about 40 mm to about 100 mm. The transition length can also be from about 50 mm to about 80 mm. Further, the transition length can be about 60 mm.

Prior to implantation, the occlusive device 100 may be cooled, for example cryogenically cooled. Upon delivery into the treated aneurysm or body space, the cold temperature of the occlusive device 100 will promote formation of thrombus in the aneurysm or body space. Instead of or in addition to such pre-cooling, the proximal section 102 or other portions of the occlusive device 100 may be coated with or adhered to a material that reacts endothermically with blood or other bodily fluids or materials. Upon delivery into the treated aneurysm or body space, the reactive material will react endothermically and chill the adjacent blood or other anatomy, thereby promoting the formation of thrombus in the aneurysm or body space. Instead of or in addition to the above-mentioned approaches to cooling, a hypotube may be provided that extends from the occlusive device 100 proximally out of the patient, and employed to deliver a coolant such as chilled saline to the implanted occlusive device 100, to chill the device and/or surrounding anatomy and promote thrombus formation. Such a hypotube may alternatively or additionally be used to deliver other materials to the implanted occlusive device 100 (e.g., into the braid lumen), including embolic materials such as microspheres or an embolic liquid.

Instead of the disclosed proximal section 102, a woven tubular structure may be employed for the proximal section 102 of the occlusive device 100. As another alternative, the proximal section 102 can comprise a laser-cut or photoetched stent in place of a braid or woven tube, or a tube formed from one or more non-woven fibers, e.g., long fibers that are pressed or otherwise bonded together into a tubular or sheet material. As yet another alternative, a highly compliant balloon of suitable length and diameter may be employed as the proximal section 102, and inflated with saline or other suitable fluid after delivery into the aneurysm or body space being treated.

The braid, weave, stent, etc. employed as the proximal section 102 may be covered along some or all of its length with a tubular polymeric membrane. The membrane may have pores formed in it so as to impart a desired level of thrombogenicity and/or resistance to blood flow. Instead of or in addition to such a membrane, thrombogenic materials can be employed as coatings, additives or otherwise in the occlusive device 100 or the proximal section 102, for example gold, platinum, platinum-iridium alloy, or fibrin. Where a braid is employed, the braid wire metals may be selected to maximize the electrical currents (and any resulting thrombogenicity) that arise from galvanic interactions at the crossings between wires of different metals.

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. An aneurysm therapy system, comprising, in combination:
   a catheter having a proximal end, a distal end, and a lumen extending between the proximal and distal ends, wherein the distal end of the catheter is configured to be positioned at or near an aneurysm; and
   an occlusive device, disposed within the lumen and configured to reside in the aneurysm to restrict fluid flow within the aneurysm, the occlusive device comprising:
      a distal section comprising a coil having an outer diameter, a coil length extending from a proximal end of the coil to a distal end of the coil, and a coil flexibility, the coil distal end being a free, terminal distal end of the coil;
      a self-expanding braided proximal section comprising a closed distal end and a free, terminal proximal end, the braided proximal section having (i) a radially compressed state with a first diameter when positioned within the delivery lumen and (ii) a radially expanded state with a second diameter, greater than the coil diameter, when unconstrained, (iii) a braid length greater than the coil length, and (iv) a braid flexibility less than the coil flexibility per unit length; and
      a tubular transition member, coupled to the coil proximal end and to the closed distal end of the braided proximal section, the transition member having (i) a transition length greater than or equal to the coil length, (ii) a transition flexibility less than the coil flexibility per unit length, and (iii) a cross-sectional profile that is less than an expanded cross-sectional profile of the braided proximal section,
   wherein the occlusive device is disposed within the catheter lumen such that the proximal section is proximal of the distal section along a longitudinal dimension of the occlusive device so that, during delivery of the occlusive device to the aneurysm, the distal section emerges from the distal end of the catheter before the proximal section, and
   wherein the proximal section is configured to expand to the expanded cross-sectional profile during advancement out of the distal end of the catheter, and the distal section is configured to distribute, along at least a portion of the coil length, a force of the advancement along an aneurysm interior wall.

2. The system of claim 1, wherein the coil outer diameter is substantially constant.

3. The system of claim 1, wherein the distal section is configured to abut the aneurysm interior wall to direct the distal most proximal section as the proximal section is advanced into the aneurysm.

4. The system of claim 1, wherein the first diameter is substantially the same as the coil diameter when the proximal section is in the delivery lumen.

5. The system of claim 1, wherein the distal section comprises a curved distal end.

6. The system of claim 5, wherein a maximum radius of curvature of the distal section is less than a maximum radius of curvature of the proximal section.

7. The system of claim 1, wherein the proximal section has a secondary preset, three-dimensional shape when in the radially expanded state.

8. The system of claim 1, wherein the braid length is from about 50 mm to about 150 mm.

9. The system of claim 1, wherein the coil length is from about 30 mm to about 40 mm.

10. The system of claim 1, wherein the second diameter is from about 2.8 to about 5.8 times the first diameter, and the first diameter is from about 0.017 inches and about 0.021 inches.

11. The system of claim 1, wherein the proximal section comprises a first bend within a first plane and a second bend out of the first plane.

12. The system of claim 1, wherein a wall of the proximal section comprises pores having an average pore size from about 25 microns to about 250 microns.

13. The system of claim 1, further comprising a shaping member extending within the proximal section and coupled to the proximal section.

14. The system of claim 1, wherein the proximal section is tubular.

15. The system of claim 1, wherein at least a portion of the transition member is tapered.

* * * * *